United States Patent
Hibbard

(10) Patent No.: US 12,226,657 B2
(45) Date of Patent: Feb. 18, 2025

(54) PREDICTING RADIOTHERAPY CONTROL POINTS USING PROJECTION IMAGES

(71) Applicant: Elekta, Inc., Atlanta, GA (US)

(72) Inventor: Lyndon Stanley Hibbard, St. Louis, MO (US)

(73) Assignee: Elekta, Inc., Atlanta, GA (US)

( * ) Notice: Subject to any disclaimer, the term of this patent is extended or adjusted under 35 U.S.C. 154(b) by 376 days.

(21) Appl. No.: 17/596,263

(22) PCT Filed: Jun. 28, 2019

(86) PCT No.: PCT/US2019/039830
§ 371 (c)(1),
(2) Date: Dec. 6, 2021

(87) PCT Pub. No.: WO2020/256750
PCT Pub. Date: Dec. 24, 2020

(65) Prior Publication Data
US 2022/0305291 A1    Sep. 29, 2022

Related U.S. Application Data

(60) Provisional application No. 62/864,188, filed on Jun. 20, 2019.

(51) Int. Cl.
*A61N 5/10*    (2006.01)

(52) U.S. Cl.
CPC ......... *A61N 5/1045* (2013.01); *A61N 5/1031* (2013.01); *A61N 5/1039* (2013.01);
(Continued)

(58) Field of Classification Search
CPC .. A61N 5/1045; A61N 5/1031; A61N 5/1039; A61N 5/1049; A61N 5/1075; A61N 5/1084; A61N 5/1047
See application file for complete search history.

(56) References Cited

U.S. PATENT DOCUMENTS

| | | |
|---|---|---|
| 9,042,620 B2 | 5/2015 | Kohlberger et al. |
| 11,077,320 B1 | 8/2021 | Hibbard |
| (Continued) | | |

FOREIGN PATENT DOCUMENTS

| | | |
|---|---|---|
| AU | 2019452405 | 12/2022 |
| CH | 709788 | 12/2015 |
| (Continued) | | |

OTHER PUBLICATIONS

Krishnamurthy et al., Using Artificial Intelligence for Optimization of the Processes and Resource Utilization in Radiotherapy, Nov. 17, 2022, JCO Glob Oncol. vol. 8, pp. 1-10. (Year: 2022).*
(Continued)

*Primary Examiner* — Christine S. Kim
(74) *Attorney, Agent, or Firm* — Schwegman Lundberg & Woessner, P.A.

(57) ABSTRACT

Systems and methods are disclosed for generating radiotherapy treatment machine parameters based on projection images of a target anatomy. The systems and methods include receiving an image depicting an anatomy of a subject; generating a first projection image based on the received image that represents a view of the anatomy from a first gantry angle of the radiotherapy treatment machine; applying a machine learning model to the first projection image to estimate a first graphical aperture image representation of multi-leaf collimator (MLC) leaf positions at the first gantry angle and the radiation intensity at that angle, the machine learning model being trained to establish a relationship between projection images representing different views of a patient anatomy and respective graphical aperture image representations of the MLC leaf positions at different gantry angles corresponding to the different views; and generating radiotherapy treatment machine parameters based on the first graphical aperture image representation.

25 Claims, 15 Drawing Sheets

(52) U.S. Cl.
CPC ......... *A61N 5/1049* (2013.01); *A61N 5/1075* (2013.01); *A61N 5/1084* (2013.01)

(56) References Cited

U.S. PATENT DOCUMENTS

| | | |
|---|---|---|
| 11,517,768 B2 | 12/2022 | Hibbard |
| 11,896,847 B2 | 2/2024 | Hibbard |
| 2005/0013406 A1 | 1/2005 | Dyk et al. |
| 2008/0064953 A1 | 3/2008 | Falco et al. |
| 2008/0298550 A1 | 12/2008 | Otto |
| 2012/0014507 A1 | 1/2012 | Wu et al. |
| 2012/0136194 A1 | 5/2012 | Zhang et al. |
| 2012/0230572 A1 | 9/2012 | Kohlberger et al. |
| 2013/0142310 A1 | 6/2013 | Fahimian et al. |
| 2014/0031603 A1 | 1/2014 | Robar et al. |
| 2016/0129282 A1 | 5/2016 | Yin et al. |
| 2016/0140300 A1 | 5/2016 | Purdie et al. |
| 2016/0213948 A1 | 7/2016 | Renne |
| 2016/0217595 A1 | 7/2016 | Han et al. |
| 2017/0177812 A1 | 6/2017 | Sjolund |
| 2018/0078784 A1 | 3/2018 | Schnarr |
| 2018/0154179 A1 | 6/2018 | Ollila et al. |
| 2018/0185672 A1 | 7/2018 | Ramezanzadeh Moghadam |
| 2018/0315188 A1 | 11/2018 | Tegzes et al. |
| 2019/0030370 A1 | 1/2019 | Hibbard |
| 2019/0192880 A1 | 6/2019 | Hibbard |
| 2019/0318474 A1 | 10/2019 | Han |
| 2019/0333219 A1 | 10/2019 | Xu et al. |
| 2019/0333623 A1 | 10/2019 | Hibbard |
| 2021/0244971 A1 | 8/2021 | Hibbard |
| 2021/0308487 A1 | 10/2021 | Hibbard |

FOREIGN PATENT DOCUMENTS

| | | |
|---|---|---|
| CN | 1530151 | 9/2004 |
| CN | 102316930 A | 1/2012 |
| CN | 103961182 A | 8/2014 |
| CN | 104933245 A | 9/2015 |
| CN | 105120955 A | 12/2015 |
| CN | 105354611 A | 2/2016 |
| CN | 105358217 A | 2/2016 |
| CN | 107708808 | 2/2018 |
| CN | 109843377 A | 6/2019 |
| CN | 110944717 A | 3/2020 |
| CN | 112041026 A | 12/2020 |
| CN | 111494810 | 10/2021 |
| CN | 115361998 | 11/2022 |
| CN | 114206438 | 5/2024 |
| EP | 2605828 A2 | 6/2013 |
| EP | 3010585 A1 | 4/2016 |
| EP | 3658231 | 4/2022 |
| EP | 3986544 | 7/2023 |
| JP | 2004240394 | 8/2004 |
| JP | 2011502010 A | 1/2011 |
| JP | 2017538195 | 12/2017 |
| JP | 2018533138 | 11/2018 |
| JP | 7307822 | 7/2023 |
| WO | WO-2014205128 A1 | 12/2014 |
| WO | WO-2015193776 A1 | 12/2015 |
| WO | WO-2016023786 A1 | 2/2016 |
| WO | WO-2016081916 A1 | 5/2016 |
| WO | WO-2018048507 A1 | 3/2018 |
| WO | WO-2018048575 A1 | 3/2018 |
| WO | WO-2019023142 A1 | 1/2019 |
| WO | 2019056134 | 3/2019 |
| WO | WO-2019212804 A1 | 11/2019 |
| WO | WO-2020256750 A1 | 12/2020 |
| WO | WO-2021159143 A1 | 8/2021 |

OTHER PUBLICATIONS

Zhao et al., Artificial intelligence in image-guided radiotherapy: a review of treatment target localization, 2021, Quant Imaging Med Surg vol. 11, pp. 4881-4894. (Year: 2021).*

Shan et al., Synergizing medical imaging and radiotherapy with deep learning, Jun. 22, 2020, Mach. Learn.: Sci. Technol.vol. 1 (2020), pp. 1-25 (Year: 2020).*

"Australian Application Serial No. 2019452405, First Examination Report mailed Nov. 14, 2022", 2 pgs.

"Australian Application Serial No. 2019452405, Response filed Nov. 16, 2022 to First Examination Report mailed Nov. 14, 2022", Claims not amended in response filed, 1 pg.

"German Application Serial No. 2021-575992, Notification of Reasons for Refusal mailed Nov. 22, 2022", With English translation, 5 pgs.

"U.S. Appl. No. 17/304,500, Notice of Allowance mailed Sep. 28, 2023", 9 pgs.

"Chinese Application Serial No. 201980099082.0, Office Action mailed Sep. 25, 2023", w English Translation, 13 pgs.

"U.S. Appl. No. 15/658,484, Advisory Action mailed Nov. 18, 2021", 4 pgs.

"U.S. Appl. No. 15/658,484, Examiner Interview Summary mailed Sep. 1, 2021", 2 pages.

"U.S. Appl. No. 15/658,484, Final Office Action mailed Mar. 25, 2021", 47 pgs.

"U.S. Appl. No. 15/658,484, Final Office Action mailed Sep. 21, 2021", 60 pages.

"U.S. Appl. No. 15/658,484, Non Final Office Action mailed Jun. 3, 2020", 30 pgs.

"U.S. Appl. No. 15/658,484, Non Final Office Action mailed Jun. 15, 2021", 46 pages.

"U.S. Appl. No. 15/658,484, Non Final Office Action mailed Dec. 1, 2020", 30 pgs.

"U.S. Appl. No. 15/658,484, Response filed Mar. 1, 2021 to Non Final Office Action mailed Dec. 1, 2020", 10 pgs.

"U.S. Appl. No. 15/658,484, Response filed May 25, 2021 to Final Office Action mailed Mar. 25, 2021", 10 pgs.

"U.S. Appl. No. 15/658,484, Response filed Sep. 10, 2021 to Non Final Office Action mailed Jul. 15, 2021", 12 pages.

"U.S. Appl. No. 15/658,484, Response filed Nov. 9, 2021 to Final Office Action mailed Sep. 21, 2021", 13 pgs.

"U.S. Appl. No. 16/784,919, Corrected Notice of Allowability mailed May 19, 2021", 4 pgs.

"U.S. Appl. No. 16/784,919, Corrected Notice of Allowability mailed Jun. 30, 2021", 4 pgs.

"U.S. Appl. No. 16/784,919, Notice of Allowance mailed Apr. 15, 2021", 10 pgs.

"Australian Application Serial No. 2017324627, First Examination Report mailed Jun. 11, 2019", 4 pgs.

"Australian Application Serial No. 2017324627, Response filed Jul. 17, 2019 to First Examination Report mailed Jun. 11, 2019", 22 pgs.

"Australian Application Serial No. 2017324627, Subsequent Examiners Report mailed Sep. 11, 2019", 11 pgs.

"Australian Application Serial No. 2018307739, First Examination Report mailed Oct. 14, 2020", 5 pgs.

"Australian Application Serial No. 2018307739, Response filed Jan. 20, 2021 First Examination Report mailed Oct. 14, 2020", 29 pgs.

"Australian Application Serial No. 2019262835, First Examination Report mailed Sep. 28, 2021", 3 pages.

"Beam's Eye View", Wikipedia https://en.wikipedia.org/wiki/Beam%27s_eye_view, (Accessed on Mar. 13, 2020), 1 pg.

"Chinese Application Serial No. 201780062011.4, Office Action mailed Apr. 21, 2021", With English translation, 22 pages.

"Chinese Application Serial No. 201780062011.4, Office Action mailed Jul. 30, 2020", w/ English translation, 23 pgs.

"Chinese Application Serial No. 201780062011.4, Response filed Jul. 2, 2021 to Office Action mailed Apr. 21, 2021", With English claims, 19 pages.

"Chinese Application Serial No. 201780062011.4, Response filed Dec. 11, 2020 to Office Action mailed Jul. 30, 2020", w/ English claims, 20 pgs.

"Chinese Application Serial No. 201880049758.0, Office Action mailed Mar. 3, 2021", w/ English translation, 22 pgs.

"Chinese Application Serial No. 201880049758.0, Office Action mailed Sep. 15, 2021", With English translation, 22 pages.

(56) References Cited

OTHER PUBLICATIONS

"Chinese Application Serial No. 201880049758.0, Response filed Jun. 30, 2021 to Office Action mailed Mar. 3, 2021", With English claims, 19 pages.

"Conditional Generative Adversarial Nets in TensorFlow", Agustinus Kristiadi's Blog, [Online]. Retrieved from the Internet: <URL: https://wiseodd.github.io/techblog/2016/12/24/conditional-gan-tensorflow/ >, 6 pgs.

"European Application Serial No. 17755011.8, Communication Pursuant to Article 94(3) EPC mailed May 6, 2021", 6 pgs.

"European Application Serial No. 17755011.8, Communication pursuant to Article 94(3) EPC mailed Jul. 1, 2020", 4 pgs.

"European Application Serial No. 17755011.8, Office Action mailed Jan. 14, 2020", 3 pgs.

"European Application Serial No. 17755011.8, Response filed Jan. 7, 2021 to Communication pursuant to Article 94(3) EPC mailed Jul. 1, 2020", 24 pgs.

"European Application Serial No. 17755011.8, Response filed Sep. 16, 2021 to Communication Pursuant to Article 94(3) EPC mailed May 6, 2021", 16 pages.

"European Application Serial No. 17755011.8, Response to Communication pursuant to Rules 161(1) and 162 EPC filed Mar. 20, 2020", 10 pgs.

"European Application Serial No. 18752372.5 Response to Communication pursuant to Rules 161(1) and 162 EPC filed Sep. 16, 2020", 16 pgs.

"European Application Serial No. 18752372.5, Communication Pursuant to Article 94(3) EPC mailed Mar. 2, 2021", 3 pgs.

"European Application Serial No. 18752372.5, Response filed Mar. 25, 2021 to Communication Pursuant to Article 94(3) EPC mailed Mar. 2, 2021", 18 pgs.

"European Application Serial No. 19727774.2, Response to Communication pursuant to Rules 161(1) and 162 EPC filed Jun. 18, 2021", 32 pages.

"Imagenet", Stanford University Vision Lab, Accessed from Internet on Nov. 9, 2018 http://www.image-net.org/, (2016), 1 pg.

"International Application Serial No. PCT/US2017/046608, International Preliminary Report on Patentability mailed Mar. 21, 2019", 8 pgs.

"International Application Serial No. PCT/US2017/046608, International Search Report mailed Jan. 15, 2018", 6 pgs.

"International Application Serial No. PCT/US2017/046608, Invitation to Pay Add'l Fees and Partial Search Report mailed Nov. 8, 2017", 7 pages.

"International Application Serial No. PCT/US2017/046608, Written Opinion mailed Jan. 15, 2018", 6 pgs.

"International Application Serial No. PCT/US2018/043320, International Preliminary Report on Patentability mailed Feb. 6, 2020", 9 pgs.

"International Application Serial No. PCT/US2018/043320, International Search Report mailed Oct. 29, 2018", 6 pgs.

"International Application Serial No. PCT/US2018/043320, Written Opinion mailed Oct. 29, 2018", 7 pgs.

"International Application Serial No. PCT/US2019/028720, International Preliminary Report on Patentability mailed Nov. 12, 2020", 8 pgs.

"International Application Serial No. PCT/US2019/028720, International Search Report mailed Oct. 16, 2019", 4 pgs.

"International Application Serial No. PCT/US2019/028720, Written Opinion mailed Oct. 16, 2019", 8 pgs.

"International Application Serial No. PCT/US2019/039830, International Search Report mailed Mar. 13, 2020", 4 pgs.

"International Application Serial No. PCT/US2019/039830, Written Opinion mailed Mar. 13, 2020", 5 pgs.

"International Application Serial No. PCT/US2021/070119, International Search Report mailed May 19, 2021", 5 pgs.

"International Application Serial No. PCT/US2021/070119, Written Opinion mailed May 19, 2021", 6 pgs.

"Japanese Application Serial No. 2019-513074, Office Action mailed Jan. 28, 2020", w/ English Translation, 4 pgs.

"Japanese Application Serial No. 2019-513074, Response filed Feb. 25, 2020 to Office Action mailed Jan. 28, 2020", w/ English claims, 11 pgs.

"Japanese Application Serial No. 2020-503934, Notification of Reasons for Refusal mailed Mar. 2, 2021", w/ English translation, 10 pgs.

"Japanese Application Serial No. 2020-503934, Response filed Jun. 25, 2021 to Notification of Reasons for Refusal mailed Mar. 2, 2021", With English claims, 12 pages.

"Ray Tracing (graphics)", Wikipedia https://en.wikipedia.org/wiki/Ray_tracing_(graphics), (2019), 15 pgs.

"Russian Federation Application Serial No. 2019110153, Office Action mailed Nov. 11, 2019", w/English Translation, 13 pgs.

"Russian Federation Application Serial No. 2019110153, Response filed Dec. 13, 2019 to Office Action mailed Nov. 11, 2019", w/ English Claims, 70 pgs.

"VRad Deep Learning Algorithm Successfully Identifies Potential Intracranial Hemorrhaging (product announcement", https://www.vrad.com, Retrieved from internet: https://www.itnonline.com/content/vrad-deep-learning-algorithm-successfully-identifies-potential-intracranial-hemorrhaging, (Dec. 14, 2015), 2 pgs.

Abadi, Martin, et al., "Tensorflow: Large-scale machine learning on heterogeneous distributed systems", arXiv preprint arXiv:1603.04467, (2016), 19 pgs.

Androsova, E E, "Application of recursive recurrent neural networks", New information technologies in automated systems (with English translation), (2016), 18 pages.

Appenzoller, Lindsey M., et al., "Predicting dose-volume histograms for organs-at-risk in IMRT planning", Medical physics 39.12, (2012), 7446-7461.

Appenzoller, Lindsey M., et al., "Predicting dose-volume histograms for organs-at-risk in IMRT planning", Med. Phys. 39 (12), (Dec. 2012), pp. 7446-7461.

Babier, A, et al., "Knowledge-based automated planning with three-dimensional generative adversarial networks", Medical Physics, (Dec. 21, 2018), 15 pgs.

Bishop, Christopher M., "Pattern Recognition and Machine Learning", Springer-Verlag New York, (2006), 758 pgs.

Breedveld, Sebastiaan, et al., "The equivalence of multi-criteria methods for radiotherapy plan optimization", Physics in Medicine & Biology 54.23, (2009), 7199-7209.

Breedveld,, Sebastiaan, et al., "The equivalence of multi-criteria methods for radiotherapy plan optimization", Phys. Med. Biol. 54 (2009), (Nov. 17, 2009), pp. 7199-7209.

Bukovsky, Ivo, et al., "A Fast Neural Network Approach to Predict Lung Tumor Motion during Respiration for Radiation Therapy Applications", BioMed Research International vol. 2015, Article ID 489679, (2015), 3 pgs.

Chris, McIntosh, et al., "Fully automated treatment planning for head and neck radiotherapy using a voxel-based dose prediction and dose mimicking method", Physics in Medicine & Biology, vol. 62, No. 15, XP055416743, (Sep. 2, 2016), 5926-5944.

Creswell, Antonia, et al., "Generative Adversarial Networks: An Overview", IEEE Signal Processing Magazine 35.1, (2018), 53-65.

Dobler, Barbara, et al., "Direct machine parameter optimization for intensity modulated radiation therapy (IMRT) of oropharyngeal cancer—a planning study", Journal of Applied Clinical Medical Physics, vol. 10, No. 4, (Fall 2009), pp. 4-15.

Georg, D, et al., "Patient-specific IMRT verification using independent fluence-based dose calculation software: experimental benchmarking and initial clinical experience", Physics in Medicine and Biology, vol. 52, (2007), 4981-4992.

Glassner, A S, "An Introduction to Ray Tracing", Morgan-Kauffman Part 2 out of 2, (1989), 176 pgs.

Glassner, A S, "An Introduction to Ray Tracing", Morgan-Kauffman Part 1 out of 2, (1989), 177 pgs.

Goodfellow, Ian, et al., "Deep learning", vol. 1. Cambridge: MIT press, (2016), 802 pgs.

Goodfellow, Ian, et al., "Generative Adversarial Nets", Advances in Neural Information Processing Systems 27, Curran Associates, Inc., (Jun. 10, 2014), 9 pgs.

Goodfellow, Ian, "NIPS 2016 tutorial: Generative adversarial networks", arXiv preprint arXiv:1701.00160, (2016), 57 pgs.

(56) References Cited

OTHER PUBLICATIONS

Gulliford, S, et al., "Generating compensation designs for tangential breast irradiation with artificial neural networks", Physics n Medicine and Biology, vol. 47, (2002), 277-288.
Hardemark, Bjorn, et al., "Direct machine parameter optimization", Philips Medical Systems part Royal Philips Electronics whitepaper, (2004), 8 pgs.
Hastie, Trevor, et al., "The elements of statistical learning: data mining, inference, and prediction", Springer series in statistics, (2001), 764 pgs.
He, Kaiming, et al., "Identity mappings in deep residual networks", European Conference on Computer Vision. Springer, Cham, (2016), 15 pgs.
Hernandez-Davila, V, et al., "Determination of neuron fluence-to-dose conversion coefficients by means of artificial neural networks", Applied Radiation and Isotopes, vol. 83, (2014), 249-251.
Hesse, Christopher, "Image-to-Image Translation in Tensorflow Make discriminators do your work for you", [Online]. Retrieved from the Internet: <URL: https://affinelayer.com/pix2pix/>, (Jan. 25, 2017), 12 pgs.
Hibbard, Lyndon, et al., "Adversarial Prediction of Radiotherapy Treatment Machine Parameters", Advances in Intelligent Data Analysis XIX; [Lecture Notes in Computer Science; Lect.Notes Computer], Springer International Publishing, Cham,, (Oct. 1, 2020), 85-94.
Hua, K L, et al., "Computer-aided classification of lung nodules on computed tomography images via deep learning technique", Onco Targets and Therapy. vol. 8, (2015), 2015-2022.
Ibragimov, B., et al., "Development of a Novel Deep Learning Algorithm for Autosegmentation of Clinical Tumor Volume and Organs at Risk in Head and Neck Radiation Therapy Planning", S226 International Journal of Radiation Oncology Biology Physics, (Oct. 1, 2016), p. 1147.
Ibragimov, B., et al., "Machine-Learning Based Segmentation of Organs at Risks for Head and Neck Radiotherapy Planning", [Online]. Retrieved from the Internet:<URL: http://onlinelibrary.wiley.com/doi/10.1118/1.4958186/full>, (Jun. 2016), 1 pg.
Isola, Phillip, et al., "Image-to-Image Translation with Conditional Adversarial Networks", arXiv:1611.07004 [cs.CV], (Nov. 22, 2017), 17 pgs.
Johnson, Hans J, et al., "The ITK Software Guide", (Jul. 25, 2019), 997 pgs.
Kak, A C, et al., "Principles of Computerized Tomographic Imagining Chapter 1", SIAM Philadelphia, (2001), 4 pgs.
Kak, A C, et al., "Principles of Computerized Tomographic Imagining Chapter 2", SIAM Philadelphia, (2001), 43 pgs.
Kak, A C, et al., "Principles of Computerized Tomographic Imagining Chapter 3", SIAM Philadephia, (2001), 64 pgs.
Kak, A C, et al., "Principles of Computerized Tomographic Imagining Chapter 4", SIAM Philadelphia, (2001), 63 pgs.
Kak, A C, et al., "Principles of Computerized Tomographic Imagining Chapter 5", SIAM Philadelphia, (2001), 25 pgs.
Kak, A C, et al., "Principles of Computerized Tomographic Imagining Chapter 6", SIAM Philadelphia, (2001), 71 pgs.
Kak, A C, et al., "Principles of Computerized Tomographic Imagining Chapter 7", SIAM Philadelphia, (2001), 22 pgs.
Kak, A C, et al., "Principles of Computerized Tomographic Imagining Chapter 8", SIAM Philapelphia, (2001), 26 pgs.
Kak, A C, et al., "Principles of Computerized Tomographic Imagining Index", SIAM Philadelphia, (2001), 6 pgs.
Kak, A C, et al., "Principles of Computerized Tomographic Imagining Introduction", SIAM Philadelphia, (2001), 9 pgs.
Kalantzis, G, et al., "Toward IMRT 2D dose modeling using artificial neural networks: A feasibility study", Medical Physics, vol. 38, (10), (2011), 5807-5817.
Kang, John, et al., "Machine Learning Approaches for Predicting Radiation Therapy Outcomes: A Clinician's Perspective", International Journal of Radiation Oncology Biology Physics, (Jul. 27, 2015), pp. 1127-1135.
Krizhevsky, Alex, et al., "Imagenet classification with deep convolutional neural networks", Advances in neural information processings systems, (2012), 1-9.
Krizhevsky, Alex, et al., "Imagenet classification with deep convolutional neural networks", Advances in neural information processing systems, (2012), 9 pgs.
Kunze-Busch, M., et al., "Efficient SIB-IMRT planning of head and neck patients with Pinnacle—DMPO", Medicamundi 51/2+3 Nov. 2007, (Nov. 2007), pp. 95-99.
Lecun, Yann, et al., "Deep Learning", Nature vol. 521, (May 28, 2015), pp. 436-444.
Lecun, Yann, et al., "Deep learning", Nature, vol. 521. 7553, (2015), 436-444.
McIntosh, C, et al., "Contextual Atlas Regression Forests: Multiple-Atlas-Based Automated Dose Prediction in Radiation Therapy", IEEE Transactions on Medical Imaging, (2016), 15 pgs.
Miao, Shun, et al., "Real-Time 2D/3D Registration Via CNN Regression", Cornell University arXiv.org > cs > arXiv:1507.07505, IEEE 13th International Symposium on Biomedical Imaging (ISBI), Prague, (2016), 5 pgs.
Mirza, Mehdi, et al., "Conditional generative adversarial nets", arXiv preprint arXiv:1411.1784, (2014), 7 pgs.
Murphy, K P, "Machine Learning: a Probabilistic Perspective", MIT Press, Cambridge, MA, USA Part 1 out of 2, (2012), 549 pgs.
Murphy, Kevin P, "Machine Learning A Probabilistic Perspective", MIT Press, Cambridge, MA, USA Part 2 out of 2, (2012), 549 pgs.
Nguyen, D, et al., "A feasibility study for predicting optimal radiation therapy dose distributions of prostate cancer patients from patient anatomy using deep learning", Scientific Reports www.nature.com/scientificreports, (Jan. 31, 2019), 10 pgs.
Nguyen, Dan, et al., "Dose Prediction with U-net: A Feasibility Study for Predicting Dose Distributions from Contours using Deep Learning on Prostate IMRT Patients", arXiv preprint arXiv:1709.09233, (2017), 17 pgs.
Nie, Dong, et al., "Estimating CT Image from MRI Data Using 3D Fully Convolutional Networks", (Sep. 27, 2016), 9 pgs.
Park, Seonyeong, et al., "Intra and Inter Fractional Variation Prediction of Lung Tumors Using Fuzzy Deep Learning", IEEE journal of Transitional Engineering in Health and Medicine, (Jan. 8, 2016), 12 pgs.
Rafid, Mahmood, et al., "Automated Treatment Planning in Radiation Therapy using Generative Adversarial Networks", Arxiv.Org, Cornell University Library, 201 Olin Library Cornell University Ithaca, NY 14853, XP081113459, (Jul. 17, 2018), 15 pgs.
Rit, S, et al., "The Reconstruction Toolkit (RTK), an open-source cone-beam CT reconstruction toolkit based on the Insight Toolkit (ITK)", (2013), 5 pgs.
Romeijn, Edwin H, et al., "A unifying framework for multi-criteria fluence map optimization models", Phys. Med. Biol. 49 (2004), (May 4, 2004), pp. 1991-2013.
Ronneberger, Olaf, et al., "U-Net Convolutional Networks for Biomedical Image Segmentation", Computer Science Department and BIOSS Centre for Biological Signalling Studies, University of Freiburg, Germany, (May 18, 2015), 234-241.
Ronneberger, Olaf, et al., "U-net: Convolutional networks for biomedical image segmentation", International Conference on Medical image computing and computer-assisted intervention. Springer, Cham, (2015), 1-8.
Shin, H-C, et al., "Interleaved text/image deep mining on a very large-scale radiology database.", Proceedings of the IEEE Conference on Computer Vision and Pattern Recognition, (2015), 1090-1099.
Shin, Hoo-Chang, et al., "Learning to Read Chest X-Rays: Recurrent Neural Cascade Model for Automated Image Annotation", National Institutes of Health, Bethesda, 20892-1182, (Mar. 28, 2016), 14 pgs.
Shirashi, S, et al., "Knowledge-based prediction of three-dimensional dose distributions for external beam radiotherapy", Medical Physics, 43(1), (2015), 378-287.
Shirley, P, et al., "Fundamentals of Computer Graphics", Chapter 10 Ray Tracing AK Peters, (2005), 785 pgs.
Syeda-Mahmood, Tanveer, et al., "Multimodal Learning for Clinical Decision Support and Clinical Image-Based Procedures", 10th

(56) References Cited

OTHER PUBLICATIONS

International Workshop, ML-CDS 2020 and 9th International Workshop, CLIP 2020 Held in Conjunction with MICCAI 2020, 147 pages.
Tseng, Huan-Hsin, et al., "Deep reinforcement learning for automated radiation adaptation in lung cancer", Medical physics 44.12, (2017), 6690-6705.
Unkelbach, Jan, et al., "Optimization approaches to volumetric modulated arc therapy planning", Am. Assoc. Phys. Med. 42 (3), (Mar. 2015), 12 pgs.
Wachowicz, K, et al., "On the direct acquisition of beam's-eye-view images in MRI for integration with external beam radiotherapy", Physics in Medicine, (2018), 11 pgs.
Wu, Binbin, et al., "Patient geometry-driven information retrieval for IMRT treatment plan quality control", Am Assoc Phys Med 36 12, (Nov. 6, 2009), 9 pgs.
Wu, Binbin, et al., "Patient geometry-driven information retrieval for IMRT treatment plan quality control", Medical physics 36.12, (2009), 5497-5505.
Yu, D, et al., "Automatic Speech Recognition: A Deep Learning Approach", Springer, (2015), 329 pgs.
Zarepisheh, Masoud, et al., "A DVH-guided IMRT optimization algorithm for automatic treatment planning and adaptive radiotherapy replanning", Medical physics 41.6Part1, (2014), 061711-1-061711-14.
Zarepisheh, Masoud, et al., "A multicriteria framework with voxel dependent parameters for radiotherapy treatment plan optimization", Am. Assoc. Phys. Med.41 (4), (Apr. 2014), 11 pgs.
Zhu, Jun-Yan, et al., "Unpaired Image-to-Image Translation using Cycle-Consistent Adversarial Networks", IEEE International Conference on Computer Vision, (2017), 10 pgs.
Zhu, N, et al., "Deep Convolutional Neural Network Image Matching for Ultrasound Guidance in Radiotherapy", [Online], Retrieved from the Internet: <URL: http://onlinelibrary.wiley.com/doi/10.1118/1.4955603/abstract>, (Jun. 2016), 2 pgs.
Zhu, Xiaofeng, et al., "A planning quality evaluation tool for prostate adaptive IMRT based on machine learning", Am. Assoc. Phys. Med. 38 2, (Feb. 2011), pp. 719-726.
Zhu, Xiaofeng, et al., "A planning quality evaluation tool for prostate adaptive IMRT based on machine learning", Medical physics 38.2, (2011), 719-726.
Zuley, M L, et al., "Applying machine learning to radiotherapy planning for head & neck cancer", [Online] Retrieved from the Internet <URL:https://deepmind.com/blog/applying-machine-learning-radiotherapy-planning-head-neck-cancer/>, (Aug. 30, 2016), 3 pgs.
"U.S. Appl. No. 15/658,484, Notice of Allowance mailed Aug. 5, 2022", 10 pgs.
"U.S. Appl. No. 15/658,484, Corrected Notice of Allowability mailed Aug. 18, 2022", 2 pgs.
"International Application Serial No. PCT US2021 070119, International Preliminary Report on Patentability mailed Aug. 18, 2022", 8 pgs.
"Japanese Application Serial No. 2021-135351, Notification of Reasons for Refusal mailed Jul. 19, 2022", w English translation, 9 pgs.
"U.S. Appl. No. 17/304,500, Non Final Office Action mailed Feb. 13, 2023", 10 pgs.
"Japanese Application Serial No. 2021-135351, Examiners Decision of Final Refusal mailed Feb. 21, 2023", With English machine translation, 3 pgs.
"Japanese Application Serial No. 2021-575992, Response filed Feb. 11, 2023 to Notification of Reasons for Refusal mailed Nov. 22, 2022", w English Claims, 14 pgs.
"European Application Serial No. 21709317.8, Response to Communication pursuant to Rules 161 and 162 filed Mar. 8, 2023", 16 pgs.
"U.S. Appl. No. 17/304,500, Response filed May 12, 2023 to Non Final Office Action mailed Feb. 13, 2023", 11 pgs.
"Chinese Application Serial No. 201880049758.0, Response filed Nov. 28, 2021 to Office Action mailed Sep. 15, 2021", w English Claims, 21 pgs.
"International Application Serial No. PCT US2019 039830, International Preliminary Report on Patentability mailed Dec. 30, 2021", 7 pgs.
"Chinese Application Serial No. 201880049758.0, Decision of Rejection mailed Apr. 20, 2022", W English Translation, 22 pgs.
"U.S. Appl. No. 15/658,484, Response filed May 18, 2022 to Non Final Office Action mailed Mar. 4, 2022", 13 pgs.
"European Application Serial No. 19740293.6, Response to Communication pursuant to Rules 161 and 162 filed Jun. 13, 2022", 14 pgs.
"Chinese Application Serial No. 201880049758.0, Response filed Jun. 16, 2022 to Decision of Rejection mailed Apr. 20, 2022" With English machine translation, Claims not amended in response filed, 15 pgs.
U.S. Appl. No. 15/658,484, filed Jul. 25, 2017, Systems and Methods for Determining Radiation Therapy Machine Parameter Settings.
U.S. Appl. No. 16/784,919 U.S. Pat. No. 11,077,320, filed Feb. 7, 2020, Adversarial Prediction of Radiotherapy Treatment Plans.
U.S. Appl. No. 17/304,500, filed Jun. 22, 2021, Adversarial Prediction of Radiotherapy Treatment Plans.
"U.S. Appl. No. 17/304,500, Non Final Office Action mailed Jun. 15, 2023", 8 pgs.
"U.S. Appl. No. 17/304,500, Response filed Sep. 12, 2023 to Non Final Office Action mailed Jun. 15, 2023", 11 pgs.
"Chinese Application Serial No. 201880049758.0, Office Action mailed Feb. 9, 2022", w English translation, 10 pgs.
"U.S. Appl. No. 15/658,484, Non Final Office Action mailed Mar. 4, 2022", 55 pgs.
"Chinese Application Serial No. 201880049758.0, Response filed Mar. 16, 2022 to Office Action mailed Feb. 9, 22", w English Claims, 20 pgs.
"Chinese Application Serial No. 202180026513.8, Office Action mailed Jun. 21, 2024", With English Machine Translation, 14 pgs.
"Chinese Application Serial No. 202180026513.8, Response filed Jul. 29, 2024 to Office Action mailed Jun. 21, 2024", W English Claims, 19 pgs.
"U.S. Appl. No. 17/304,500, Corrected Notice of Allowability mailed Jan. 12, 2024", 4 pgs.
"Chinese Application Serial No. 201980099082.0, Response filed Jan. 17, 2024 to Office Action mailed Sep. 25, 2023", w English claims, 18 pgs.

\* cited by examiner

PREDICTING RADIOTHERAPY CONTROL POINTS USING PROJECTION IMAGES

CLAIM FOR PRIORITY

This application is a U.S. National Stage Filing under 35 U.S.C. § 371 from International Application No. PCT/US2019/039830, filed on Jun. 28, 2019, and published as WO2020/256750 on Dec. 24, 2020, which claims the benefit of priority to U.S. Provisional Application No. 62/864,188, filed Jun. 20, 2019; the benefit of priority of each of which is hereby claimed herein, and which applications and publication are hereby incorporated herein by reference in their entireties.

TECHNICAL FIELD

Embodiments of the present disclosure pertain generally to determining machine parameters that direct the radiation therapy performed by a radiation therapy treatment system. In particular, the present disclosure pertains to using deep learning technologies to determine machine parameters that define a treatment plan in a radiation therapy system.

BACKGROUND

Radiation therapy (or "radiotherapy") can be used to treat cancers or other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Overview

In some embodiments, a method is provided for generating radiotherapy treatment machine parameters based on projection images. The method includes: receiving an image depicting an anatomy of a subject; generating a first projection image based on the received image that represents a view of the anatomy from a first gantry angle of the radiotherapy treatment machine; applying a trained machine learning model to the first projection image to estimate a first graphical aperture image representation of multi-leaf collimator (MLC) leaf positions at the first gantry angle, the machine learning model being trained to establish a relationship between projection images representing different views of a patient anatomy and respective graphical aperture image representations of the MLC leaf positions at different gantry angles corresponding to the different views; and generating one or more radiotherapy treatment machine parameters based on the estimated first graphical aperture image representation.

In some implementations, the machine learning model comprises a deep convolution neural network.

In some implementations, training the machine learning model is performed by adjusting one or more parameters of the machine learning model to minimize a cost function that includes a difference between predetermined sets of graphical aperture image representations of the MLC leaf positions corresponding to projection images representing different views of a patient anatomy and predicted sets of graphical aperture image representations of the MLC leaf positions at the different views.

In some implementations, the one or more parameters include at least one of a gantry angle, an MLC jaw position, an MLC leaf position, or a radiation therapy beam intensity.

In some implementations, receiving the image comprises receiving a three-dimensional image of the anatomy, further comprising generating a plurality of two-dimensional projection images including the first projection image that represent a plurality of two-dimensional views of the anatomy from a plurality of different gantry angles.

In some implementations, the plurality of projection images represents views of the anatomy from 0 degrees to 360 degrees.

In some implementations, the different gantry angles differ from one another by a predetermined amount.

In some implementations, the method includes determining a type of the radiotherapy treatment machine, wherein the one or more radiotherapy treatment machine parameters are generated based on the type of the radiotherapy treatment machine.

In some implementations, the image comprises a computed tomography (CT) image, a synthetic CT image, or a magnetic resonance (MR) image.

In some implementations, the method further comprises training the machine learning model by: obtaining the projection images representing different views of a patient anatomy from prior treatments; for each of the prior treatments: obtaining radiotherapy treatment machine parameter information representing MLC leaf positions at gantry angles corresponding to each of the different views and radiotherapy beam intensity corresponding to each of the projection images; and generating ground truth graphical aperture image representations based on the obtained radiotherapy treatment machine parameter information; aligning each of the generated ground truth graphical aperture image representations with the corresponding projection images; and adjusting one or more parameters of the machine learning model based on the paired generated ground truth graphical aperture image representations and corresponding projection images.

In some implementations, the one or more parameters of the machine learning model are adjusted by computing a deviation between a given graphical aperture image representation at a given one of the different views that is estimated based on a given projection image representing the given one of the different views with a corresponding one of the ground truth graphical aperture image representations for the given one of the different views.

In some implementations, the method includes computing a quality metric based on a comparison of the generated one or more radiotherapy treatment machine parameters with a set of parameters of a radiotherapy treatment plan.

In some implementations, the method includes computing a three-dimensional dose distribution based on the generated one or more radiotherapy treatment machine parameters.

In some implementations, the first projection image is generated by ray tracing or Fourier reconstruction.

In some embodiments, a method is provided for training a machine leaning model to estimate a graphical aperture image representation of multi-leaf collimator (MLC) leaf positions, the method comprising: obtaining a first projection image representing a first view of a patient anatomy from a previous treatment; obtaining radiotherapy treatment machine parameter information representing MLC leaf positions at a gantry angle corresponding to the first view of the first projection image; and generating a first ground truth graphical aperture image representation based on the obtained control point information; and adjusting one or more parameters of the machine learning model based on the first ground truth graphical aperture image representations and the first projection image.

In some implementations, adjusting the one or more machine learning model parameters is performed by: applying the machine learning model to the first projection image to estimate a graphical aperture image representation of the MLC leaf positions at the gantry angle corresponding to the first view; computing a deviation between the estimated graphical aperture image representation and the first ground truth graphical image representation; and adjusting one or more machine learning model parameters based on the computed deviation.

In some implementations, the radiotherapy treatment machine parameter information further includes radiotherapy beam intensity at the gantry angle, further comprising aligning the first graphical aperture image representations with the first projection image.

In some implementations, a system is provided for generating radiotherapy treatment machine parameters based on projection images, the system comprising: one or more processors for performing operations comprising: receiving an image depicting an anatomy of a subject; generating a first projection image based on the received image that represents a view of the anatomy from a first gantry angle of the radiotherapy treatment machine; applying a trained machine learning model to the first projection image to estimate a first graphical aperture image representation of multi-leaf collimator (MLC) leaf positions at the first gantry angle, the machine learning model being trained to establish a relationship between projection images representing different views of a patient anatomy and respective graphical aperture image representations of the MLC leaf positions at different gantry angles corresponding to the different views; and generating one or more radiotherapy treatment machine parameters based on the estimated first graphical aperture image representation.

In some implementations, the operations further comprise training the machine learning model by adjusting one or more parameters of the machine learning model to minimize a cost function that includes a difference between predetermined sets of graphical aperture image representations of the MLC leaf positions corresponding to projection images representing different views of a patient anatomy and predicted sets of graphical aperture image representations of the MLC leaf positions at the different views.

In some implementations, the operations further comprise receiving a three-dimensional image of the anatomy, further comprising generating a plurality of two-dimensional projection images including the first projection image that represent a plurality of two-dimensional views of the anatomy from a plurality of different gantry angles.

In some implementations, the operations further comprise training the machine learning model by: obtaining the projection images representing different views of a patient anatomy from prior treatments; for each of the prior treatments: obtaining radiotherapy treatment machine parameter information representing MLC leaf positions at gantry angles corresponding to each of the different views and radiotherapy beam intensity corresponding to each of the projection images; and generating ground truth graphical aperture image representations based on the obtained radiotherapy treatment machine parameter information; aligning each of the generated ground truth graphical aperture image representations with the corresponding projection images; and adjusting one or more parameters of the machine learning model based on the paired generated ground truth graphical aperture image representations and corresponding projection images.

In some embodiments, non-transitory machine-readable storage medium is provided that includes instructions that, when executed by one or more processors of a machine, cause the machine to perform operations comprising: receiving an image depicting an anatomy of a subject; generating a first projection image based on the received image that represents a view of the anatomy from a first gantry angle of the radiotherapy treatment machine; applying a machine learning model to the first projection image to estimate a first graphical aperture image representation of multi-leaf collimator (MLC) leaf positions at the first gantry angle, the machine learning model being trained to establish a relationship between projection images representing different views of a patient anatomy and respective graphical aperture image representations of the MLC leaf positions at different gantry angles corresponding to the different views; and generating one or more radiotherapy treatment machine parameters based on the estimated first graphical aperture image representation.

In some implementations, the operations further comprise training the machine learning model by adjusting one or more parameters of the machine learning model to minimize a cost function that includes a difference between predetermined sets of graphical aperture image representations of the MLC leaf positions corresponding to projection images representing different views of a patient anatomy and predicted sets of graphical aperture image representations of the MLC leaf positions at the different views.

In some implementations, the operations further comprise receiving a three-dimensional image of the anatomy, further comprising generating a plurality of two-dimensional projection images including the first projection image that represent a plurality of two-dimensional views of the anatomy from a plurality of different gantry angles.

In some implementations, the operations further comprise training the machine learning model by: obtaining the projection images representing different views of a patient anatomy from prior treatments; for each of the prior treatments: obtaining radiotherapy treatment machine parameter information representing MLC leaf positions at gantry angles corresponding to each of the different views and radiotherapy beam intensity corresponding to each of the projection images; and generating ground truth graphical aperture image representations based on the obtained radiotherapy treatment machine parameter information; aligning each of the generated ground truth graphical aperture image representations with the corresponding projection images; and adjusting one or more parameters of the machine learning model based on the paired generated ground truth graphical aperture image representations and corresponding projection images.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
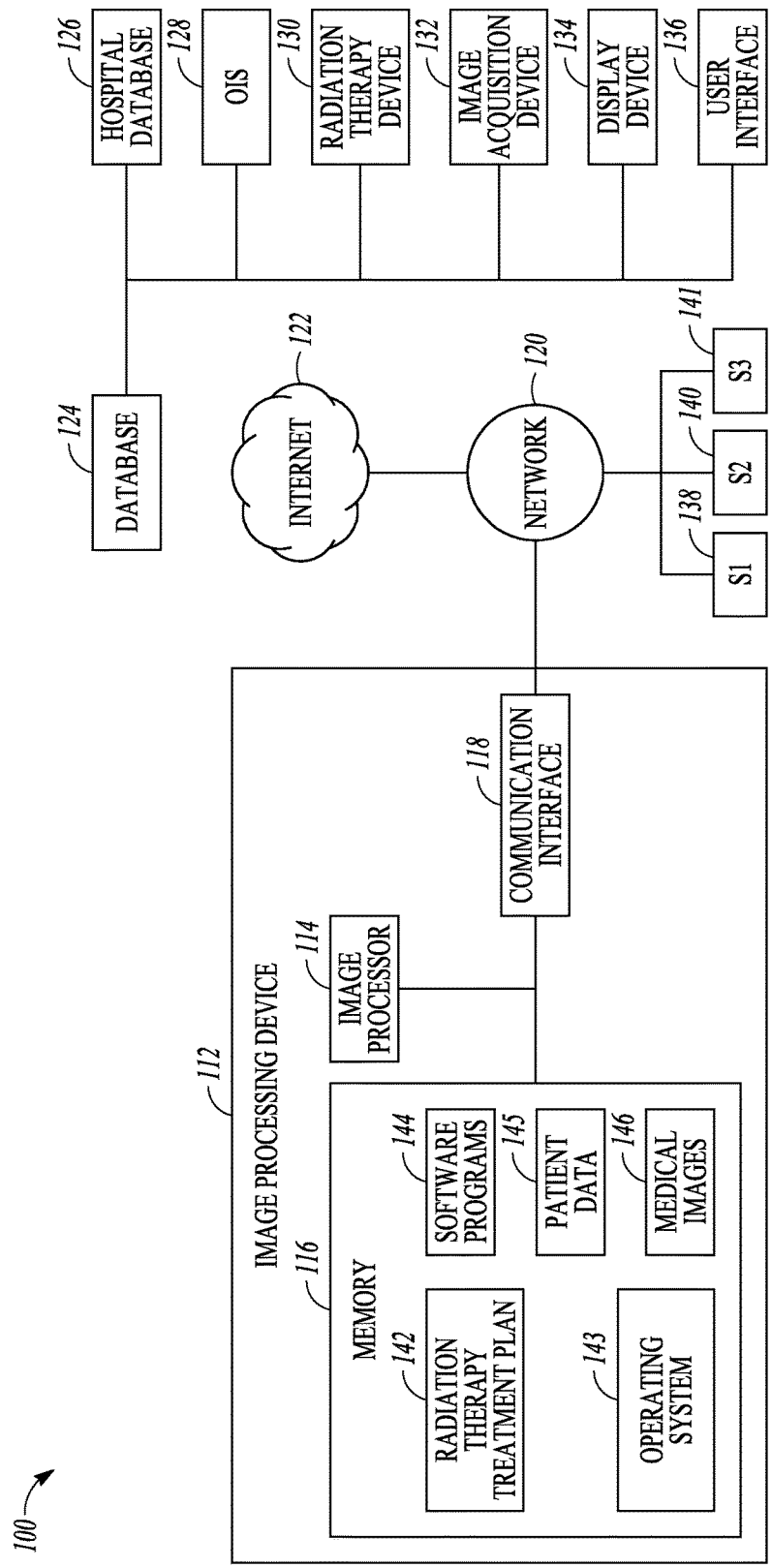
FIG. 1 illustrates an exemplary radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not be taken in a limiting sense, and the scope of the present disclosure is defined by the appended claims and their equivalents.

Intensity modulated radiotherapy (IMRT) and volumetric modulated arc therapy (VMAT) have become the standards of care in modern cancer radiation therapy. Creating individual patient IMRT or VMAT treatment plans is a trial-and-error process, weighing target dose versus OAR sparing tradeoffs, and adjusting program constraints whose effects on the plan quality metrics and the dose distribution can be very difficult to anticipate. Indeed, the order in which the planning constraints are adjusted can itself result in dose differences. Treatment plan quality depends on often subjective judgements by the planner that depend on his/her experience and skill. Even the most skilled planners still have no assurance that their plans are close to the best possible, or whether a little or a lot of effort will result in a significantly better plan.

The present disclosure includes various techniques to improve and enhance radiotherapy treatment by predicting radiotherapy treatment machine parameters (also referred to as control points) for delivering intended dose distributions based on a patient's delineated anatomy. The technical benefits include reduced radiotherapy treatment plan creation time and may result in many apparent medical treatment benefits (including improved accuracy of radiotherapy treatment, reduced exposure to unintended radiation, and the like). The disclosed techniques may be applicable to a variety of medical treatment and diagnostic settings or radiotherapy treatment equipment and devices.

The present disclosure predicts or estimates control points by training a machine learning model on training data consisting of pairs of control points and the corresponding images of a patient. These data pairs are constructed and aligned so that each element of the image data corresponds to an element of the control point data. The disclosed machine learning method then determines a mapping or relationship between the two data realms. This learned model associates the image data and the control point data without explicit reference to the physics of radiation transport or to the many details attending the creation of treatment plans from which the training data were extracted.

According to some embodiments, the disclosure directly learns (trains a machine learning model based on) the parameters of a population of exemplary treatment plans for a common diagnosis, and then uses that model to predict the treatment machine parameter settings required to deliver the intended dose distributions based only on the new patient's delineated anatomy. The treatment parameters include the linac gantry angles, beam aperture shapes through which the therapeutic radiation beams are projected at the target, and the beams' intensities, any parameter used to delivery electron or particle therapy, among others. This disclosure estimates the machine parameters to drive the treatment machine, given the image of the patient and the target and OAR delineations.

According to some embodiments, a kind of statistical learning based on deep neural networks (deep learning) is used to obtain a much more detailed model of the linkages between patient anatomies and treatment constraints and the resulting treatment machine parameter settings that would deliver the intended 3D dose distribution. Such a result is impossible with any of the earlier plan quality analyses. By employing a machine learning model, this disclosure produces a model of the treatment planning process, encapsulating the many (subjective) decisions made during plan creation and enables: the production of plan templates to initiate plan creation, the assessment of existing plans' likely quality, aid for treatment clinics lacking deep local IMRT/VMAT expertise, and fully automated treatment planning. By using deep learning to generate control points of a radiotherapy device and the implied treatment plans, computational complexity of the total plan optimization process is reduced and the time needed to create a treatment plan for a given patient is reduced.

Specifically, according to some embodiments, a machine learning model is trained to establish a relationship between a projection of a given image of a patient anatomy corresponding to a given angle of a gantry of the radiotherapy device and a graphical aperture image representation of MLC leaf positions of the radiotherapy device. The machine learning model is trained by obtaining the projection images representing different views of a patient anatomy from prior treatments; and for each of the prior treatments: obtaining control point information representing MLC leaf positions at gantry angles corresponding to each of the different views and radiotherapy beam intensity corresponding to each of the projection images to generated ground truth graphical aperture image representations based on the obtained control point information paired with the projection images. Subsequently, one or more parameters of the machine learning model are adjusted based on the paired generated ground truth graphical aperture image representations and corresponding projection images. Once trained, a new patient projection image is obtained and a corresponding graphical aperture image representation of MLC leaf positions of the radiotherapy device are estimated using the trained machine learning model. Other embodiments may include graphical representations of the beams' intensities (e.g., bar graphs) in addition to the MLC leaf positions.

In some embodiments, control points of the radiotherapy device are then computed based on the estimated graphical aperture image representation of MLC leaf positions. Namely, a reverse mapping function is utilized to generate control points (e.g., beam intensity, gantry angle, and/or MLC leaf positions of individual leaves of the MLC) to achieve a beam that corresponds to the estimated graphical aperture image representation of the MLC leaf positions. In particular, the graphical aperture image representation of MLC leaf positions identifies a resulting beam shape that is output by the radiotherapy device and the reverse mapping function is utilized to generate the control points to provide the resulting beam shape that is represented by the graphical aperture image representation of MLC leaf positions.

FIG. 1 illustrates an exemplary radiotherapy system 100 for providing radiation therapy to a patient. The radiotherapy system 100 includes an image processing device 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114. In one embodiment, the software programs 144 may convert medical images of one format (e.g., MRI) another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In yet another embodiment, the software programs 144 may generate projection images for a set of two-dimensional (2D) and/or 3D CT or MR images depicting an anatomy (e.g., one or more targets and one or more OARs) representing different views of the anatomy from a first gantry angle of the radiotherapy equipment. For example, the software programs 144 may process the set of CT or MR images and create a stack of projection images depicting different views of the anatomy depicted in the CT or MR images from various perspectives of the gantry of the radiotherapy equipment. In particular, one projection image may represent a view of the anatomy from 0 degrees of the gantry, a second projection image may represent a view of the anatomy from 45 degrees of the gantry, and a third projection image may represent a view of the anatomy from 90 degrees of the gantry. The degrees may be a position of the MLC relative to a particular axis of the anatomy depicted in the CT or MR images. The axis may remain the same for each of the different degrees that are measured.

In yet another embodiment, the software programs 144 may generate graphical aperture image representations of MLC leaf positions at various gantry angles. These graphical aperture images are also referred to as aperture images. In particular, the software programs 144 may receive a set of control points that are used to control a radiotherapy device to produce a radiotherapy beam. The control points may represent the beam intensity, gantry angle relative to the patient position, and the leaf positions of the MLC, among other machine parameters. Based on these control points, a graphical image may be generated to graphically represent the beam shape and intensity that is output by the MLC at each particular gantry angle. The software programs 144 may align each graphical image of the aperture at a particular gantry angle with the corresponding projection image at that angle that was generated. The images are aligned and scaled with the projections such that each projection image pixel is aligned with the corresponding aperture image pixel.

In yet another embodiment, the software programs 144 store a treatment planning software that includes a trained machine learning model to generate or estimate a graphical aperture image representation of MLC leaf positions at a given gantry angle for a projection image of the anatomy representing the view of the anatomy from the given gantry angle. The software programs 144 may further store a function to convert or compute machine parameters or control points for a given type of machine to output a beam from the MLC that achieves the same or similar estimated graphical aperture image representation of the MLC leaf positions. Namely, the treatment planning software may output an image representing an estimated image of the beam shape and intensity for a given gantry angle and for a given projection image of the gantry at that angle, and the function may compute the control points for a given radiotherapy device to achieve that beam shape and intensity.

In addition to the memory 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium, and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory 116. For example, the processor 114 may receive medical images 146 from the image acquisition device 132 via the communication interface 118 and network 120 to be stored in memory 116. The processor 114 may also send medical images 146 stored in memory 1116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information; or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may hydride in ore than one processor (for example, a multi-core design or a plurality of processors each having a multi-core design). The processor 114 can execute sequences of computer program instructions, stored in memory 116, to perform various operations, processes, methods that will be explained in greater detail below.

The memory device 116 can store medical images 146. In some embodiments, the medical images 146 may include one or more MRI images (e.g., 2D MRI, 3D MRI, 2D streaming MRI, four-dimensional (4D) MRI, 4D volumetric MRI, 4D cine MRI, etc.), functional MRI images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the image processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory 116. The communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 114 may communicate with database 124 to read images into memory 116 or store images from memory 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital imaging and Communications in Medicine (DIMCOM) data, projection images, graphical aperture images, etc.) that the database 124 received from image acquisition device 132. Database 124 may store data to be used by the image processor 114 when executing software program 144, or when creating radiation therapy treatment plans 142. Database 124 may store the data produced by the trained machine leaning mode, such as a neural network including the network parameters constituting the model learned by the network and the resulting predicted data. The image processing device 112 may receive the imaging data, such as a medical image 146 (e.g., 2D MRI slice images, CT images, 2D Fluoroscopy images, X-ray images, 3D MRI images, 4D MRI images, projection images, graphical aperture images, etc.) either from the database 124, the radiation therapy device 130 (e.g., an MRI-linac), and or the image acquisition device 132 to generate a treatment plan 142.

In an embodiment, the radiotherapy system 100 can include an image acquisition device 132 that can acquire medical images (e.g., MRI images, 3D MRI, 2D streaming 4D volumetric MRI, CT images, cone-Beam CT, PET images, functional MRI images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can be also stored by the image processing device 112, as medical image 146 in memory 116.

In an embodiment, for example, the image acquisition device 132 may be integrated with the radiation therapy device 130 as a single apparatus (e.g., an MRI-linac). Such an MRI-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target, such as a tumor. In some embodiments, the delineation of one or more OARs, such as healthy tissue surrounding the tumor or in close proximity to the tumor may be required. Therefore, segmentation of the OAR may be performed when the OAR is dose to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR, defining 95% of dose to the target tumor; defining that the spinal cord, brain stem, and optic structures receive ≤45Gy, ≤55Gy and ≤54Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, the image acquisition device 132 could be implemented as a virtual machine. Given the processing power, memory, and computational capability available, the entire radiotherapy system 100 could be implemented as a virtual machine.

Figure 2A:
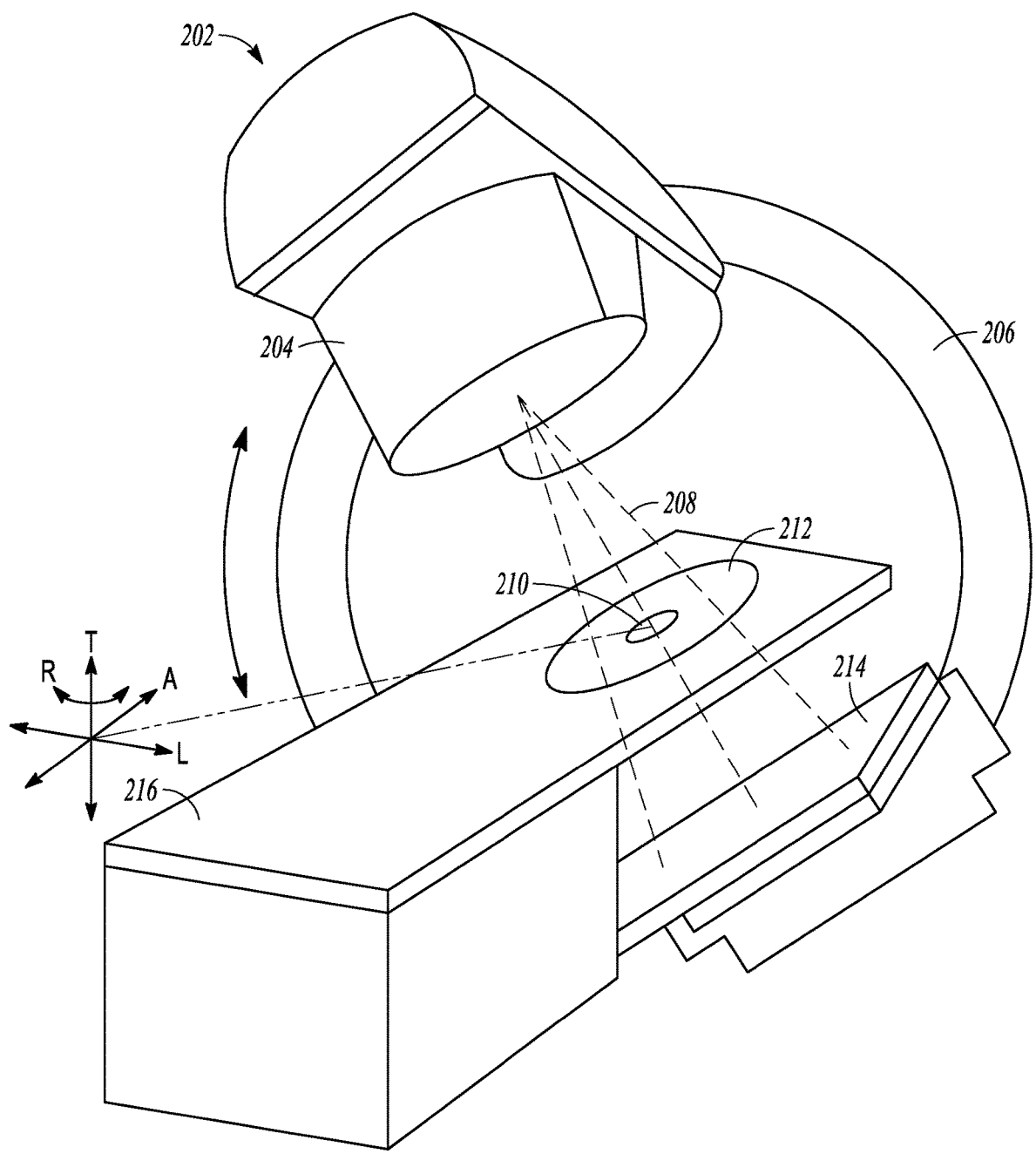
FIG. 2A illustrates an exemplary radiation therapy system that can include radiation therapy output configured to provide a therapy beam, according to some embodiments of the present disclosure.

FIG. 2A illustrates an exemplary radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC as described in the illustrative embodiment of FIG. 5, below.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 precisely can target the tumor. The MLC may be integrated and included within gantry 206 to deliver the radiation beam 208 of a certain shape.

The coordinate system (including axes A, T and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an embodiment, the imaging detector 214 can be located within a field of the therapy beam 208.

The imaging detector 214 can be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 100 or remote from it.

Figure 2B:
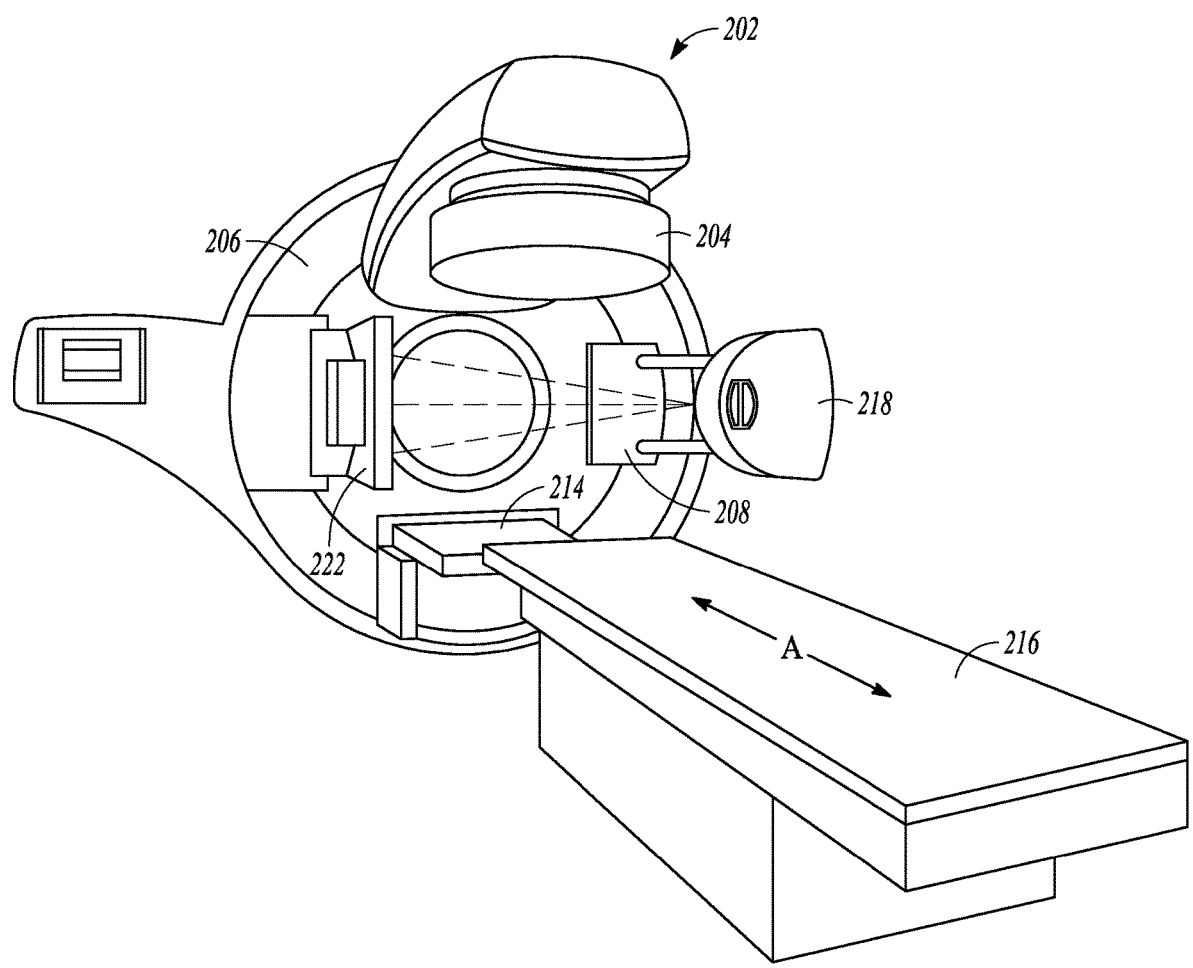
FIG. 2B illustrates an exemplary system including a combined radiation therapy system and an imaging system, such as a cone beam computed tomography (CBCT) imaging system, according to some embodiments of the present disclosure.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided, FIG. 2B illustrates an exemplary radiation therapy device 202 that may include a combined linac and an imaging system, such as can include a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

In the illustrative embodiment of FIG. 2B, the radiation therapy output 204 and the X-ray source 218 can be mounted on the same rotating gantry 206, rotationally-separated from each other by 90 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
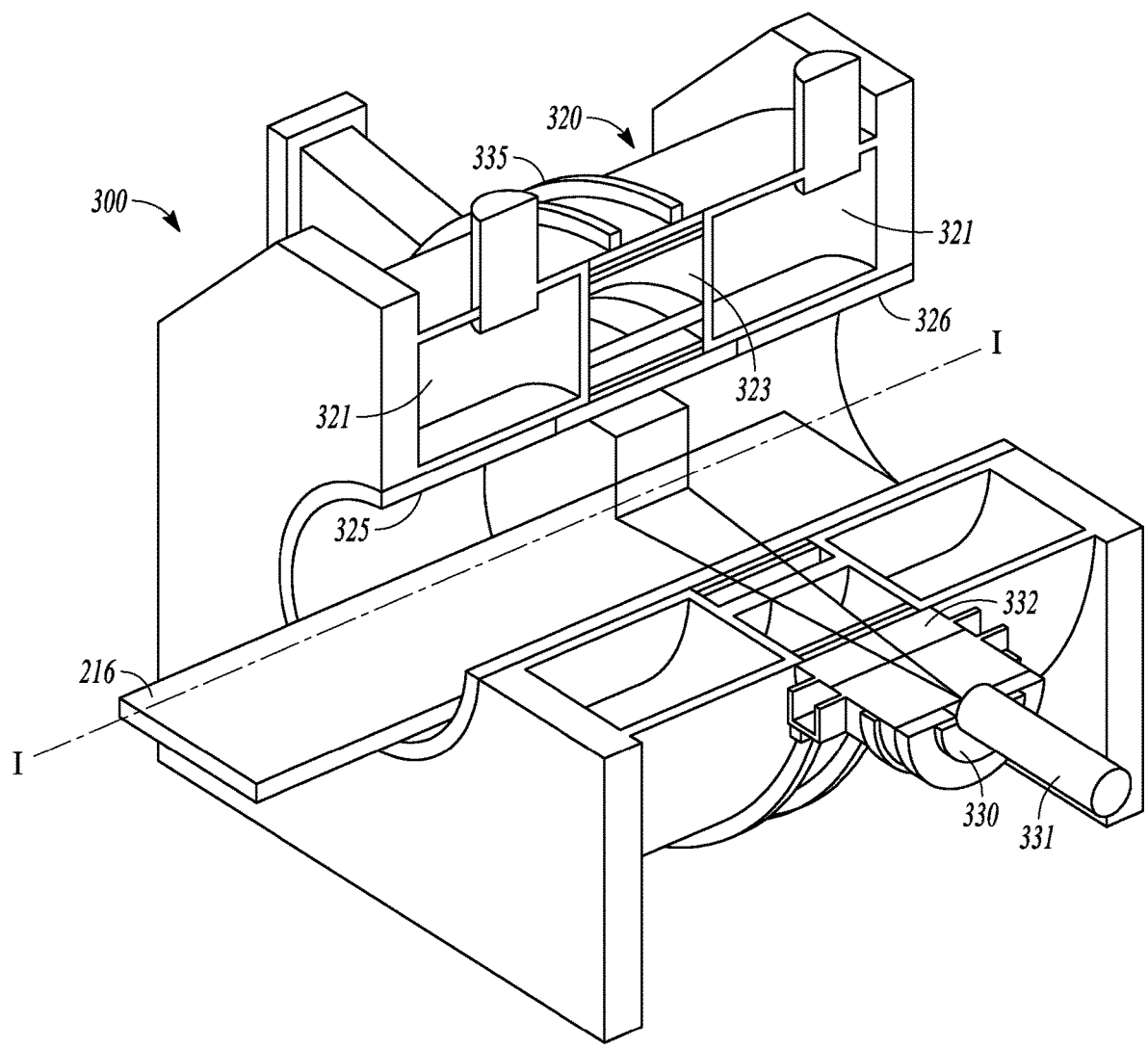
FIG. 3 illustrates a partially cut-away view of an exemplary system including a combined radiation therapy system and an imaging system, such as a nuclear magnetic resonance (MR) imaging (MRI) system, according to some embodiments of the present disclosure.
Figure 4A:
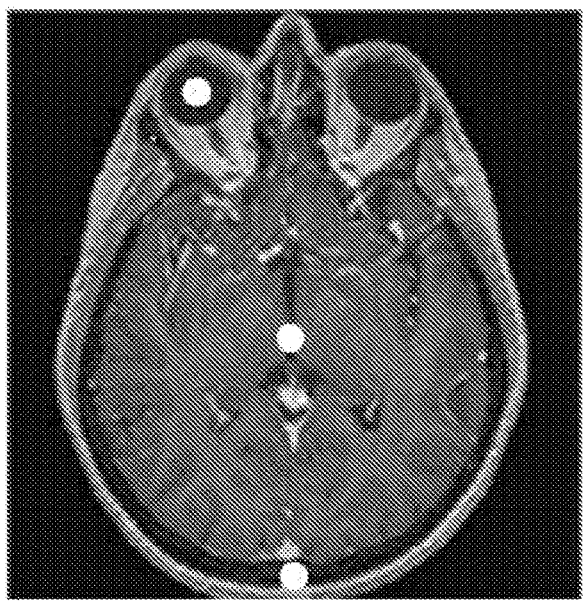
FIGS. 4A and 4B depict the differences between an exemplary MRI image and a corresponding CT image, respectively, according to some embodiments of the present disclosure.
Figure 4B:
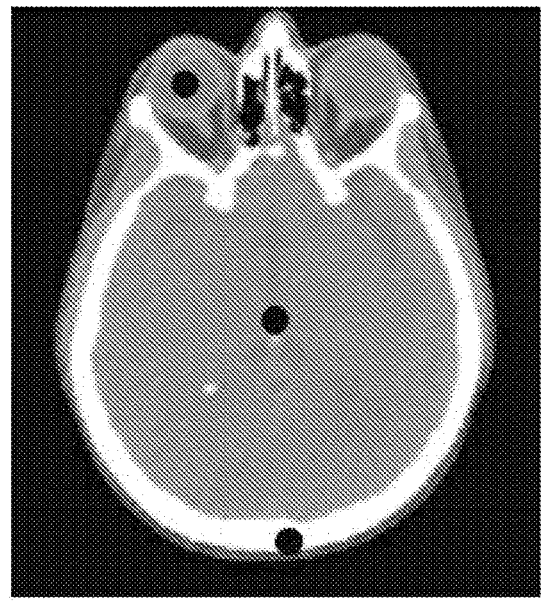

FIG. 3 depicts an exemplary radiation therapy system 300 that can include combining a radiation therapy device 202 and an imaging system, such as a nuclear MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In embodiments where magnet 321 can also include a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Figure 5:
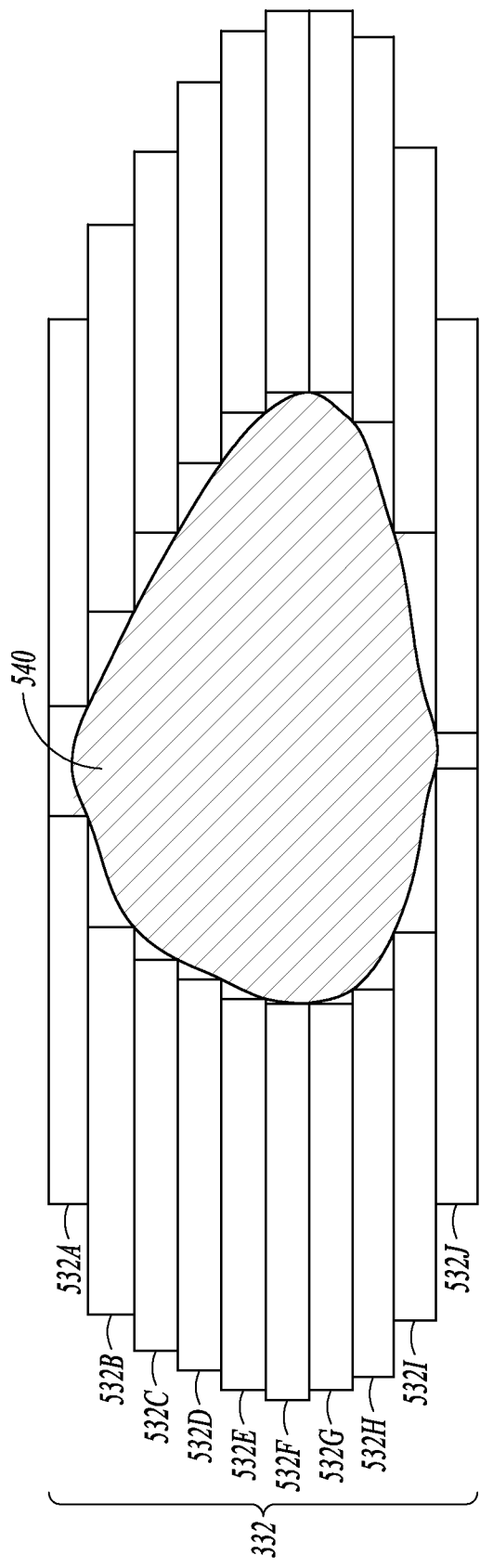
FIG. 5 illustrates an exemplary collimator configuration for shaping, directing, or modulating an intensity of a radiation therapy beam, according to some embodiments of the present disclosure.

Radiotherapy device 330 may include the radiation source 331, such as an X-ray source or a linac, and an MLC 332 (shown below in FIG. 5). Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216, when couch 216 is inserted into the treatment area. Chassis 335 may also have an attached radiation detector ((not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, add radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnetic 321 and coils 325, 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally illustrate embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient. FIG. 5 illustrates an exemplary MLC 332 that includes leaves 532A through 532J that can be automatically positioned to define an aperture approximating a tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 531J can include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 can be adjusted adaptively during a course of radiation therapy treatment, such as to establish a therapy beam that better approximates a shape or location of the tumor 540 or other target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as IMRT. The resulting beam shape that is output using the MLC 332 is represented as a graphical aperture image. Namely, a given graphical aperture image is generated to represent how a beam looks (beam shape) and its intensity after being passed through and output by MLC 332.

Figure 6:
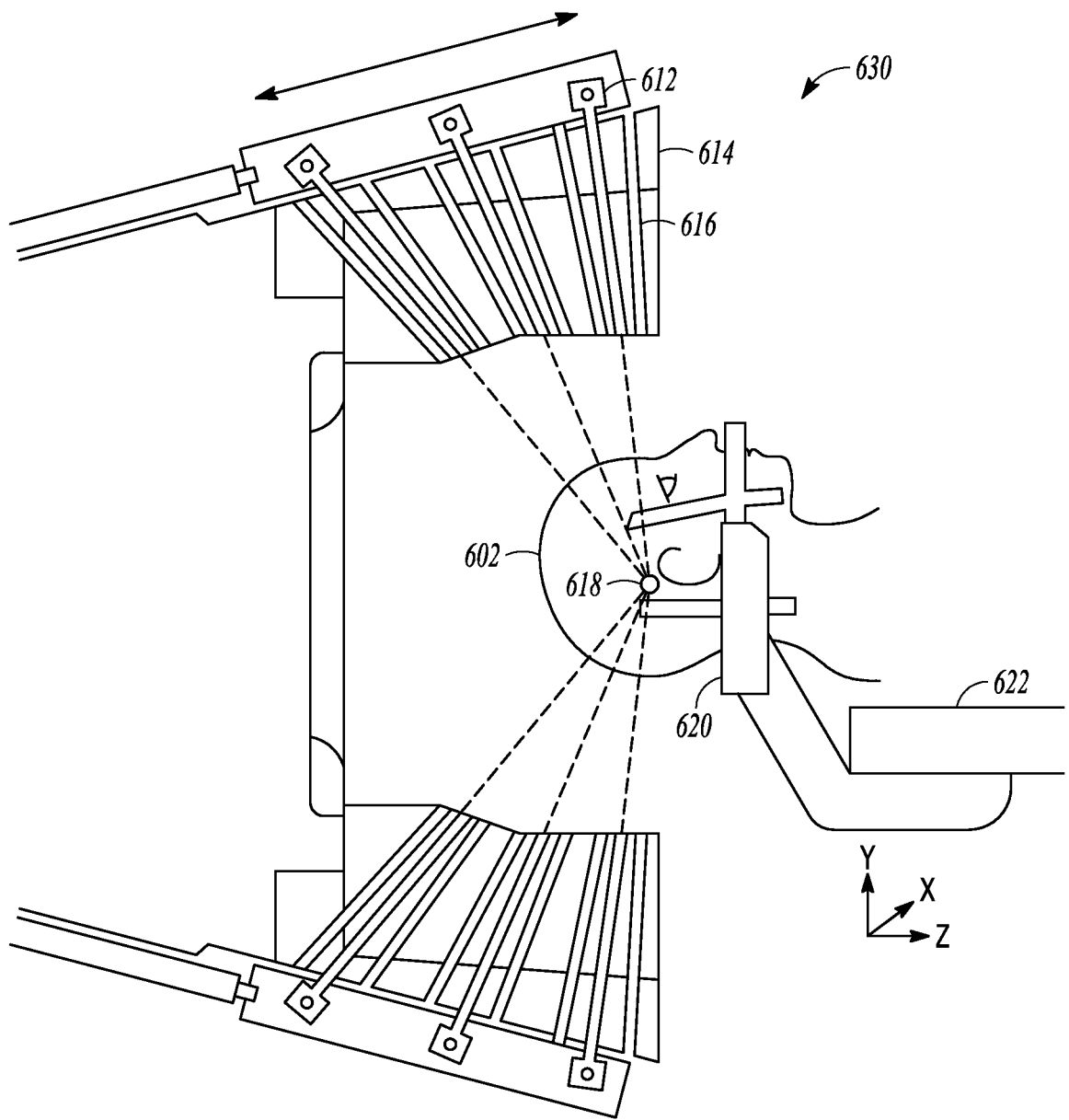
FIG. 6 illustrates an exemplary Gamma Knife radiation therapy system, according to some embodiments of the present disclosure.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

Figure 7:
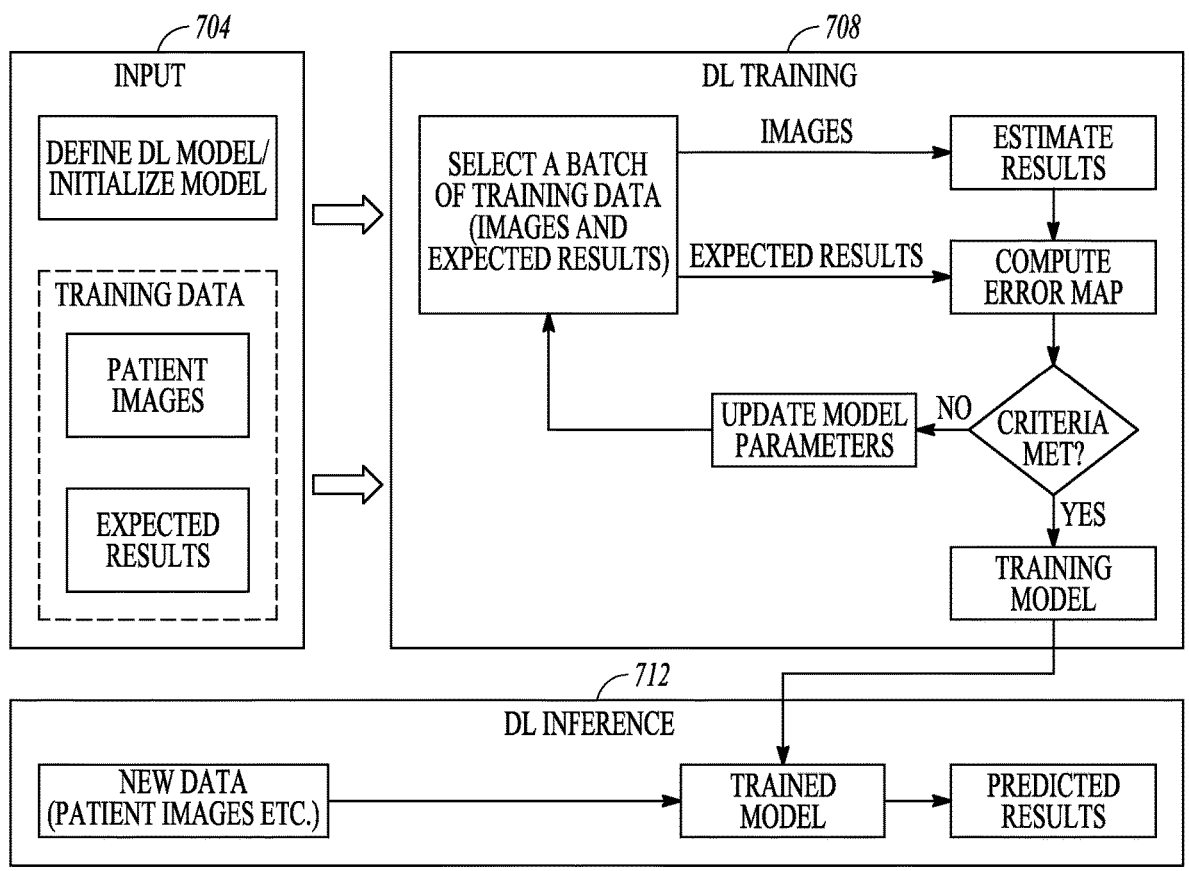
FIG. 7 illustrates an exemplary flow diagram for deep learning, according to some embodiments of the present disclosure.

FIG. 7 illustrates an exemplary flow diagram for deep learning, where a deep learning model (or a machine learning model), such as a deep convolutional neural network (DCNN), can be trained and used to determine machine parameters for a treatment plan. Inputs 704 can include a defined deep learning model having an initial set of values and training data. The training data can include patient images and expected results. The training data can also include data based on the patient images, such as one or more of anatomy label maps or signed distance maps. The training data can also include paired data including a projection image of a patient anatomy from a given angle of a gantry relative to the patient or anatomy that is paired with a graphical aperture image representation of leaves of the MLC at the given angle. The training data can include multiple of these paired images for multiple patients at any number of different gantry angles. In some cases, the training data can include 360 pairs of projection images and graphical aperture images, one for each angle of the gantry for each training patient. In some cases, 8 pairs may be included where each pair represents a different 45-degree view of the anatomy relative to the gantry.

The deep learning model can include a neural network, such as a deep convolutional neural network (DCNN). The deep learning network can be trained on medical images, such as projection images of an anatomy representing different views of the anatomy at different gantry angles from CT images, PET images, or MRI images and the corresponding graphical aperture image representation of leaves of the MLC at each of the different gantry angles. When trained, the deep learning network can produce an estimate of such graphical aperture image representation of leaves of the MLC at a particular gantry angle for a patient using only a projection image at the particular gantry angle generated based on that patient's CT or MRI image. The expected results can include estimated graphical aperture image representation of leaves of the MLC that can be used to compute control points for generating a beam shape at the corresponding gantry angle to define the delivery of radiation treatment to a patient. The control points or machine parameters can include at least one gantry angle, at least one multi-leaf collimator leaf position, and at least one aperture weight or intensity.

In some embodiments, the projection images at different gantry angles can be paired with different machine parameters at the angle. In such cases, rather than training the machine learning model to estimate the graphical aperture images for different projection images at different gantry angles, the machine learning model can be trained to estimate the machine parameters directly at each angle for a given projection image at that angle. In such, circumstances, a projection image can be generated from one or more CT or MR images of a patient anatomy representing a view of the anatomy from a given angle of the gantry. The projection image is input to the trained machine leaning model which estimates the corresponding machine parameters for that projection image for the given angle of the gantry.

During training of deep learning model 708, a batch of training data can be selected from the patient images and expected results. The selected training data can include at least one projection image of patient anatomy representing a view of the patient anatomy from a given gantry angle and the corresponding ground truth graphical aperture image and/or machine parameter data at that given gantry angle. The selected training data can include multiple projection images of patient anatomy representing views of the same patient anatomy from multiple equally spaced or non-equally-spaced gantry angles (e.g., from 0 degrees, from degrees, from 45 degrees, from 60 degrees, from 75 degrees, from 90 degrees, from 105 degrees, from 120 degrees, from 135 degrees, from 150 degrees, from 165 degrees, from 180 degrees, from 195 degrees, from 210 degrees, from 225 degrees, from 240 degrees, from 255 degrees, from 270 degrees, from 285 degrees, from 300 degrees, from 315 degrees, from 330 degrees, from 345 degrees, and/or from 360 degrees) and the corresponding ground truth graphical aperture image and/or machine parameter data at those different equally-spaced or non-equally spaced gantry angles.

The deep learning model can be applied to the selected projection images to provide estimated results (e.g., estimated graphical aperture image(s) and/or machine parameters at various gantry angles), which can then be compared to the expected results (e.g., graphical aperture image or machine parameters corresponding to the selected projection images) to compute a difference that can provide an indication of training errors. The errors can be used during a procedure called backpropagation to correct the errors in parameters of the deep learning network (e.g., layer node weights and biases), such as to reduce or minimize errors in the machine parameter or graphical aperture image estimates during subsequent trials. The errors can be compared to predetermined criteria, such as proceeding to a sustained minimum for a specified number of training iterations. If the errors do not satisfy the predetermined criteria, then model parameters of the deep learning model can be updated using backpropagation, and another batch of training data can be selected from the other projection images (of the same patient or other patients) and expected results for another iteration of deep learning model training. If the errors satisfy the predetermined criteria, then the training can be ended, and the trained model can then be used during a deep learning testing or inference stage 712 to predict machine parameters or graphical aperture image based on projection images different from the training data. The trained model can receive new projection image(s) representing views of an anatomy from a particular gantry angle and provide predicted results (e.g., machine parameters or graphical aperture image(s) for that particular gantry angle).

FIG. 7 illustrates an embodiment of a method for training a Deep Convolutional Neural Network (DCNN), such as the DCNN for determining a set of machine parameters or graphical aperture image(s) for that particular gantry angle based on at least one medical image projection depicting a view of a patient anatomy from a gantry angle. The DCNN can receive sets of medical images representing different image projections depicting views of a patient anatomy from different gantry angles. The projection images can be generated from CT images, MRI images, synthetic CT, and/or PET images. The DCNN can also receive corresponding anatomy voxel label maps and functions of labelled object signed distance maps. Machine parameters or graphical aperture image(s) for the various gantry angles depicted in the projection images can then be determined for each set of medical images. In an embodiment, the machine parameters or graphical aperture image(s) can be received together with the sets of medical projection images.

The machine parameters can include at least one gantry angle, at least one multi-leaf collimator leaf position, and at least one aperture weight or intensity. The machine parameters can be represented by the expression $Y=\{\varphi,( \ldots L_n^\varphi R_n^\varphi \ldots )^T, y^\varphi\}_k$, $k=1, \ldots, K$, where Y can represent a set of K machine parameter data objects, $\varphi$ can represent a gantry angle, $L_n^\varphi R_n^\varphi$ can represent left and right multi-leaf collimator leaf positions, and $y^\varphi$ can represent an aperture weight or intensity for a gantry angle $\varphi$. To begin network training, an iteration index can be set to an initial value of zero. A batch of training data can be formed from a subset of the received sets of medical image projections and corresponding graphical aperture image(s) for the gantry angles represented by the medical image projections. Particularly, one batch of medical image projections may represent anatomy of a first training subject from multiple gantry angles and the training data includes graphical aperture images generated based on machine parameters that were used at each of the multiple gantry angles while treating the first training subject. Another batch of medical image projections may represent anatomy of a second training subject from multiple gantry angles and the training data includes graphical aperture images generated based on machine parameters that were used at each of the multiple gantry angles while treating the second training subject.

The batch of training data can be provided to the DCNN and the DCNN parameters can be updated based thereon.

The DCNN can provide an output set of machine parameters or graphical aperture images based on current parameters of the DCNN for a given set of received media image projections. A comparison can be made between the output set of machine parameters or graphical aperture images corresponding to the received sets of medical image projections in the batch of training data (e.g., ground truth machine parameters or graphical aperture images). Corresponding error sets, where each error value can be the difference between the estimated machine parameters or graphical aperture images and the corresponding ground truth machine parameters or graphical aperture images are determined from the comparison. Parameters of the DCNN can then be updated based on the corresponding errors, such as by using backpropagation.

In an embodiment, parameters of the DCNN can be updated, such as to minimize or reduce a cost function, such as the cost function $J(\Theta^*) = \arg\min_\Theta \|Y - Y^*\|^2$, where Y can represent the machine parameters or graphical aperture images determined by the DCNN, where Y* can represent the known machine parameters or graphical aperture images corresponding to the batch of training data, and where $\Theta^*$ can represent parameters of the DCNN (e.g., layer node weights and biases as described above) corresponding to a minimized square error between Y and Y*.

In an embodiment, the cost function can probabilistic function where parameters of the DCNN can be determined according to the expression $\Theta_{OPT} = \arg\max_\Theta P(Y|X;\Theta)$, or $\Theta_{OPT} = \arg\max_\Theta \Sigma_{t \in T} \log P(Y_t|X_t;\Theta)$, where $\Theta_{OPT}$ can represent the parameters of the fully trained DCNN, and X can represent a collection of medical image projections at different gantry angles, derived from anatomy voxel label maps, or functions of the labelled object signed distance maps.

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, such as the memory device 116 of image processing device 112, and the training can be halted. If the stopping criteria are not satisfied, then the training can continue by obtaining another batch of training images from the same training subject or another training subject. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output set of machine parameters or graphical aperture images (e.g. the stopping criteria can include whether the difference between the output set of machine parameters or graphical aperture images and the machine parameters or graphical aperture images corresponding to the received sets of medical image projections in the batch of training data is smaller than a threshold). In an embodiment, the threshold can correspond to an asymptotic minimum of all errors determined. In an embodiment, the machine parameters or graphical aperture images can be presented to the DCNN in the form of images with fixed formats specifying, for example, apertures, angles, and intensity values. In an embodiment, the patient images can be pooled with machine parameters and can be presented as real arrays.

FIG. 7 illustrates a method for generating machine parameters or graphical aperture images using a trained DCNN, such as a DCNN that can be trained according to the method described above. A medical image projection of an anatomy from a given gantry angle can be received from an image acquisition device, such as image acquisition device 132. A trained DCNN model can be received from a network, such as the network 120, or from a memory, such as the memory device 116 of image processing device 112. The trained DCNN can be used to determine machine parameters or graphical aperture images for the given gantry angle from the received projection image, such as for radiation treatment planning or re-planning. In an embodiment, the trained DCNN can generate machine parameters or graphical aperture images for online applications, in real time (e.g. the trained DCNN can generate machine parameters or graphical aperture images from the received medical images in a few seconds). In an embodiment where the DCNN can be trained using machine parameters determined for intensity modulated radiotherapy, the trained DCNN can determine machine parameters for an intensity modulated radiotherapy treatment plan. In an embodiment where the DCNN can be trained using machine parameters determined for a volumetric modulated arc therapy, the trained DCNN can determine machine parameters for a volumetric modulated arc therapy treatment plan.

A motivation for predicting machine parameters or control points, using a machine learning model, is to accelerate treatment planning computations. Current, conventional treatment planning proceeds from CT or MR image through anatomy and target delineation to planning. Modern IMRT and VMAT planning uses the images and the delineated structures to define a 3D dose distribution and the machine parameters to deliver that dose distribution. The resulting clinical plan based on the CT or MR image is typically produced after two phases of numerical optimization. In the case of an MR image, an additional step is provided to convert the MR image to a synthetic CT image. The CT image pixel intensities are a function of the tissues' X-ray absorption and provide essential physics information for the treatment planning program. MR-based planning creates a synthetic CT image to provide that X-ray absorption data for planning. The first phase (e.g., Fluence Map Optimization or "FMO") produces an idealized dose distribution that satisfies the planner's requirements. The second phase (e.g., Segment Shape, Weight Optimization) creates the machine parameters for the given linac and MLC to produce a 3D dose distribution in the patient that as closely as possible agrees with the Fluence Map distribution.

The disclosed embodiments improve the quality and speed at which the treatment plans are created using control point prediction (e.g., a DL Plan Estimate). The DCNN workflows imagine DCNN segmentation of anatomy and target and the generation of synthetic CTs for MR images. DCNN training produces a model for control points based on very good treatment plans involving both phases of optimization. The control points estimated by the trained DCNN in a sense incorporate the information in both planning phases. One way in which the planning process can be shortened includes eliminating the Fluence Map phase all together and using the control point estimates as input to the second phase (Segment Shape, Weight Optimization). This speeds up the second phase computation, which speeds up the planning process.

A challenge for control point prediction based on anatomy is that the anatomy and control points have fundamentally different common representations. Anatomies are depicted by rectilinear medical images of various modalities and control points are vectors of real number parameters. Further, even if the control points' apertures are represented by, a graphical representation in an image, the orientation of the aperture does not correspond to any of the standard 2D or 3D views of anatomy. As the linac travels in an arc around the patient, the anatomy view at any moment is a projection image of the anatomy, equivalent to a plane radiograph of that anatomy at that angle. According to some embodiments, control point aperture data is re-formatted, converted to an aperture image, and aligned with the anatomy projections at the corresponding angles.

Figure 8A:
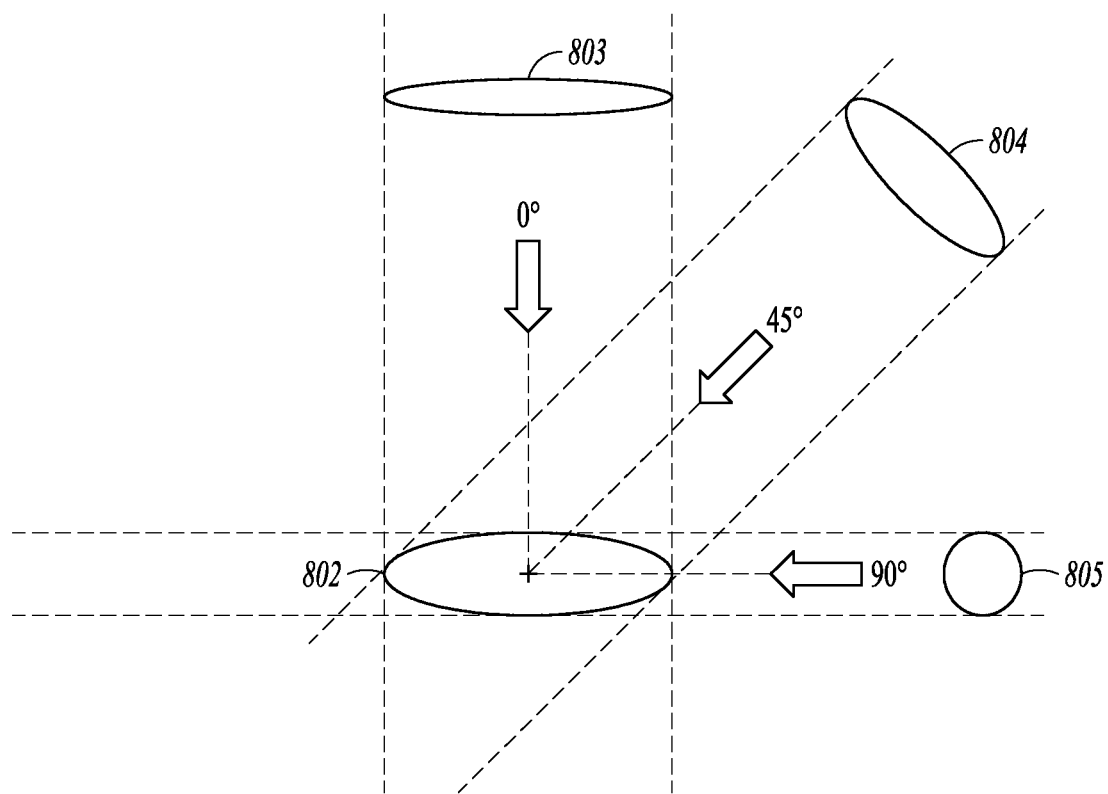
FIGS. 8A and 8B illustrate projection views from various directions, according to some embodiments of the present disclosure.

Projection views for a simple ellipse 802 are shown schematically in FIG. 8A. In FIG. 8A, the views are oriented relative the ellipse center and capture the shape and extent of the ellipse 802 as seen from each angle (e.g., 0 degrees represented by view 803, 45 degrees represented by view 804, and 90 degrees represented by view 805). For example, the view of ellipse 802 when seen from a 0-degree angle relative to the y-axis 807 of ellipse 802 is projected as view 803. For example, the view of ellipse 802 when seen from a 45-degree angle relative to the y-axis 807 of ellipse 802 is projected as view 804. For example, the view of ellipse 802 when seen from a 90-degree angle relative to the y-axis 807 of ellipse 802 is projected as view 805.

Figure 8B:
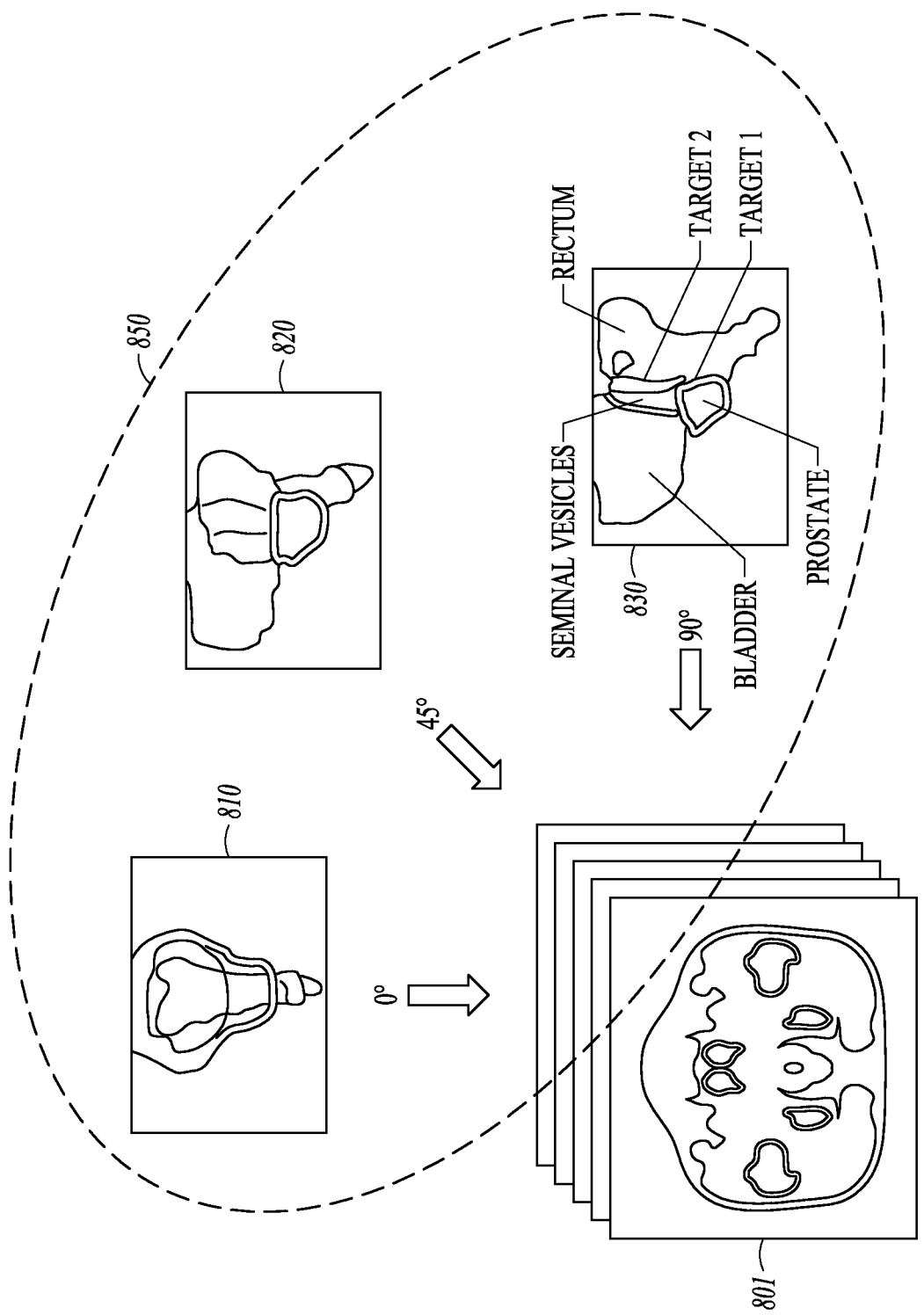

Projections of the male pelvic anatomy relative to a set of original 3D CT images 801 are shown in FIG. 8B. Selected organs at risk and target organs were contoured in the 3D CT image 801 and their voxels were assigned a constant value. Projection images 850 at selected angles (0 degrees, 45 degrees, and 90 degrees) about the central axis of the 3D CT image 801 can be obtained using the forward projection capability of a cone beam CT reconstruction program. Projection images can also be computed either by directly re-creating the projection view geometry by ray tracing or by Fourier reconstruction as in computed tomography.

For example, the projection image can be computed by tracing the path of light as pixels in an image plane and simulating the effects of its encounters with virtual objects. In some implementations, the projection image is generated by tracing a path from an imaginary eye (the MLC view or beam's eye view) through each pixel in a virtual screen and calculating the color of the object visible through it. Any other tomographic reconstruction technique can be utilized to generate the projection images from the MLC beam's eye view of the anatomy depicted in the 3D CT images 802.

For example, the set of 3D CT images 801 can be used to generate one or more views of the anatomy (e.g., the bladder, prostate, seminal vesicles, rectum, first and second targets) depicted in the 3D CT images 801. The views can be from the perspective of the MLC including the gantry of the radiotherapy device and, for simplicity with reference to FIG. 8B, the views are measured in degrees relative to the y-axis of the 3D CT images 801 and based on a distance between the anatomy depicted in the image and the MLC. Specifically, a first view 810 represents a projection of the 3D CT images 801 when viewed or seen by the gantry when the gantry is 0 degrees relative to the y-axis and is at a given distance from the anatomy depicted in the 3D CT image 801, a second view 820 represents a projection of the 3D CT images 801 when viewed or seen by the gantry when the gantry is 45 degrees relative to the y-axis and is at a given distance from the anatomy depicted in the 3D CT image 801, and a third view 830 represents a projection of the 3D CT images 801 when viewed or seen by the gantry when the gantry is 90 degrees relative to the y-axis. Any other views can be provided such as a different view at each of 360 degrees around the anatomy depicted in the 3D CT images 801.

Figure 9:
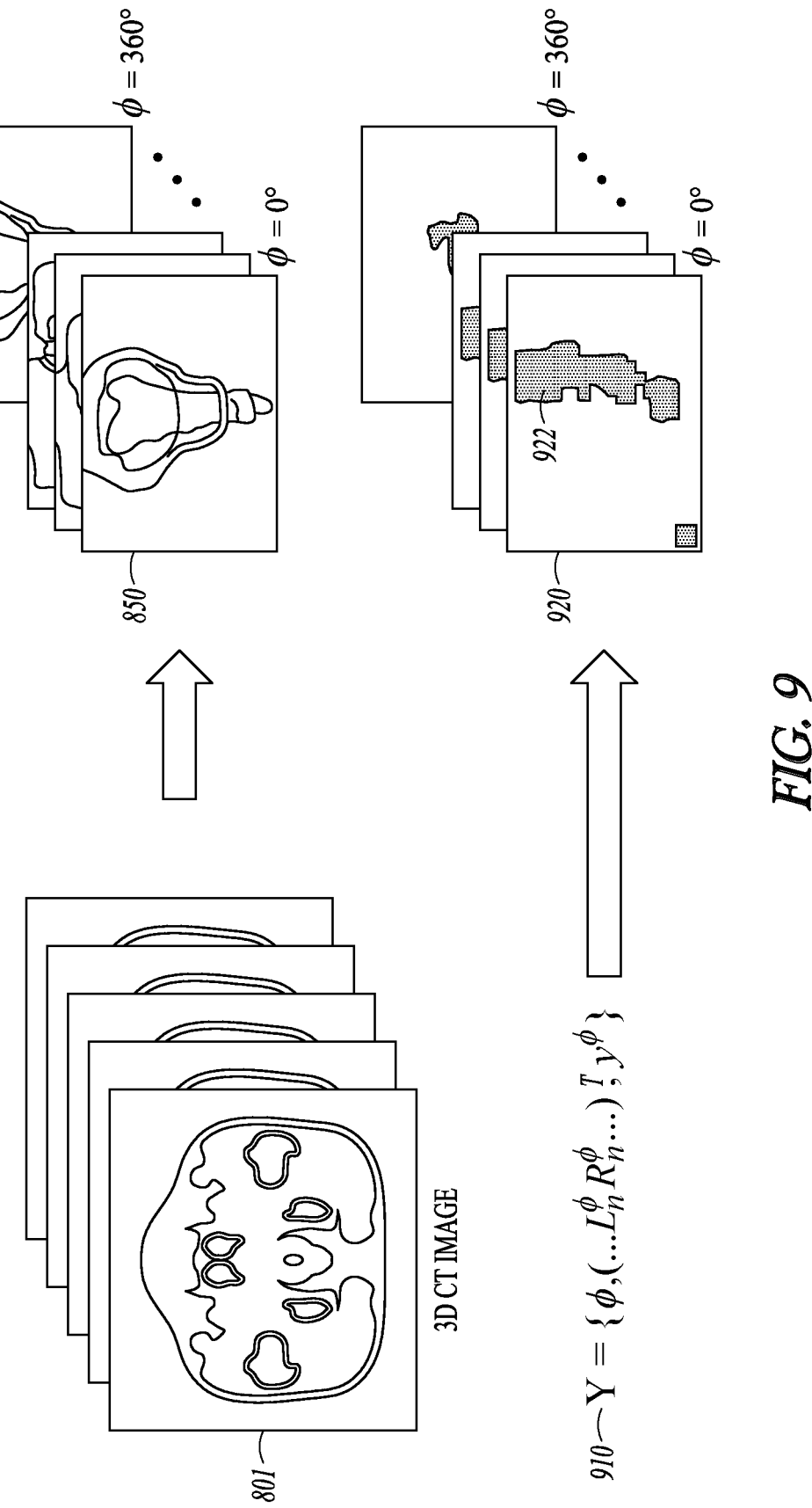
FIG. 9 illustrates an exemplary method for generating training data for deep learning, according to some embodiments of the present disclosure.

FIG. 9 illustrates an exemplary method for generating training data for deep learning, according to some embodiments of the present disclosure. Specifically, in FIG. 9 images and control point parameters are transformed into 3D image volumes. In the top portion of FIG. 9, 3D CT images 801 are converted to a stack of projection images 850 at selected angles about the central axis of the 3D CT image 801 in a similar manner as discussed in connection with FIGS. 8A and 8B. In the lower portion of FIG. 9, the control point angles, apertures, and intensities 910, corresponding to each angle of the gantry represented by the projection images 850, are recreated as graphical aperture images 920. The shaded portion 922 shows the openings between MLC left and right leaf edges that permit radiation to pass in each graphical aperture image 920. Graphical aperture images 920 are aligned and scaled with the projection images 850 such that each projection pixel is aligned with the corresponding aperture pixel that irradiates it. In some embodiment, a bar object can be presented for each graphical aperture image (e.g., at the lower left of the graphical aperture image 920). The length of this bar object encodes the radiation intensity at this control point and is estimated along with the leaf positions.

The control point parameters 910 ($Y=\{\varphi,( \ldots L_n^\varphi R_n^\varphi \ldots )^T, y^\varphi\}_k$, k=1, ..., K) represent the gantry angles, the MLC apertures at each gantry angle, and the radiation intensity at that angle. The apertures are depicted as graphical aperture images 920. Each graphical aperture image 920 is assigned and paired with a corresponding one of the anatomy projection images 850 at the same gantry angle. Each shaded portion 922 represents an opening between pairs of opposing tungsten MLC leaves (e.g., 532A-J) and it is these apertures that control the shape of the X-ray beam to cover the target to the prescribed radiation dose. The projection images 850 and the graphical aperture images 920 are scaled and aligned to ensure that each anatomy pixel in the projection images 850 is aligned with the corresponding aperture pixel irradiating that anatomy element. The construction of anatomy and control point data are represented as aligned 3D image volumes with common dimensions, pixel spacing, and origin.

Figure 10:
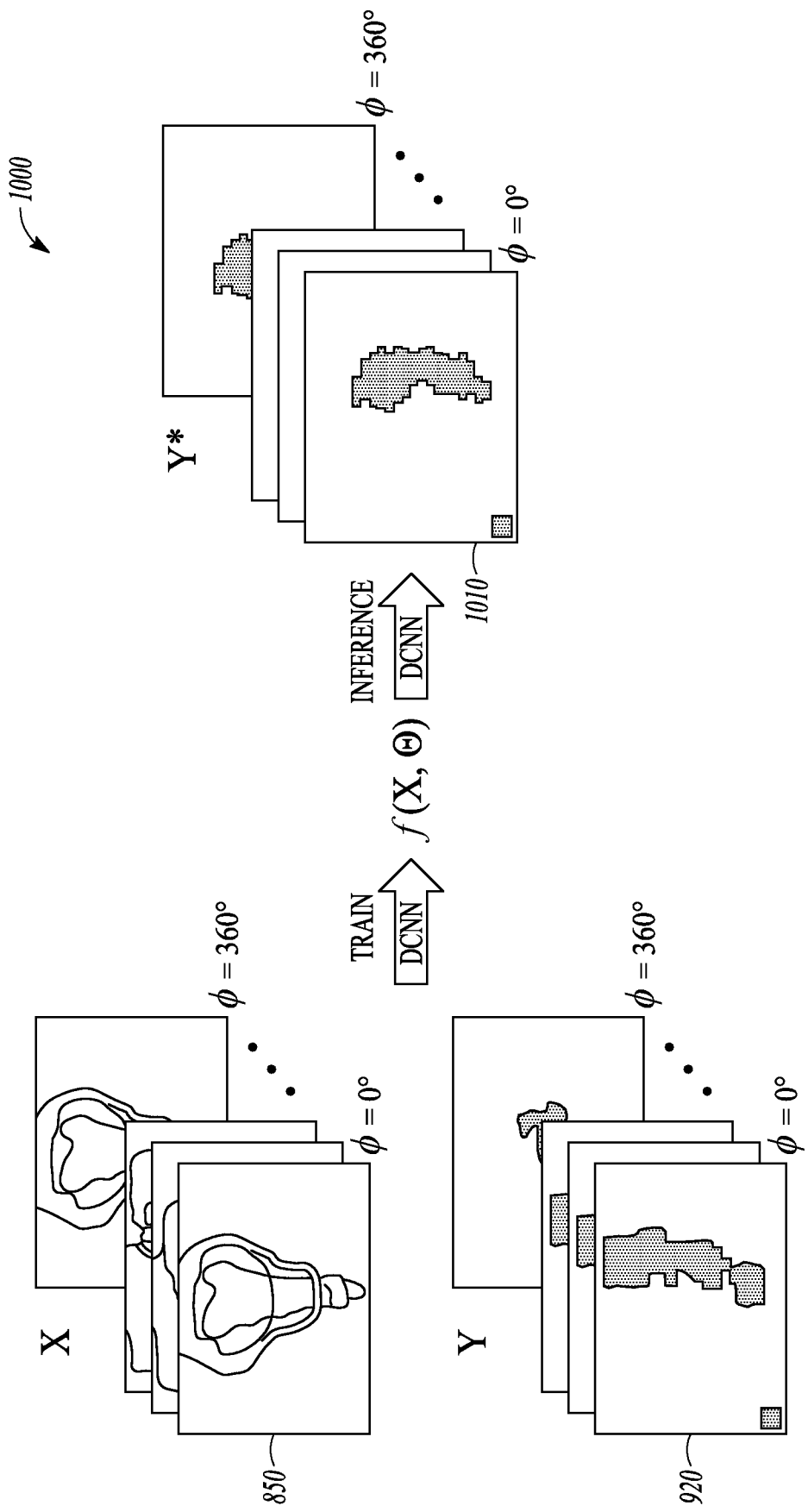
FIG. 10 illustrates an exemplary method for training deep learning using projection images and graphical representations of leaf positions, according to some embodiments of the present disclosure.

FIG. 10 illustrates an embodiment of a DCNN 1000 that can be trained using sets of known images or image functions and graphical images of known machine parameters. Once trained, the DCNN can compute estimates of graphical aperture images 1010 for one or more gantry angles for a new patient (e.g., a patient that did not contribute known images or image functions used in the training process) given only the new patient's projection images 850 at the one or more gantry angles. In an embodiment, the DCNN 1000 can include a DCNN for regression. The DCNN 1000 can be stored in a memory, such as the memory device 116 of image processing device 112. The DCNN 1000 can be comprised of (possibly many) convolutional layers, organized in blocks of layers, with each block typically operating on successively lower resolution versions of the image and control point data. Projection image data 850 and corresponding graphical aperture image data 920 can be introduced into the DCNN by convolutional layers with a kernel of width one. Each convolution layer block can be composed of at least one convolution layer and a nonlinearity layer (e.g., a rectified linear unit or ReLU layer) that can apply a non-linear function to the output of the convolution layer. Each block may also contain a batch normalization layer, a scaling layer, or other layers that may be determined, such as to provide the most accurate estimates of desired graphical aperture image values. The last layer in the last block of each set can be a pooling layer that can downsample the convolution output data by an amount (e.g., one-half) and can take the maximum of the relevant layer-node values in the output convolution layer during a process known as max-pooling. The changing shapes of each convolution block set can indicate that a spatial resolution of the image data can be decreasing (block height) while the number of parameters per layer can be increasing (block width). The arrangement of layers and the layer-set compositions can preserve the information content of the DCNN.

During network training, the graphical aperture images output using the projection images 850 can be compared to the correct graphical aperture images 920 (e.g., ground truth graphical aperture images), and the differences (e.g., errors) are used to correct the network parameters. The correction process is known as backpropagation. The network parameters can be the layer node weight coefficients and bias terms summarized as the Θ in FIG. 10 associated with the layer nodes whose values can be reset during backpropagation. Network training produces a network model or function f(X,Θ) indicated in FIG. 10. The model depends on both the input training images X and the network parameters Θ. Once trained, the network model can produce the graphical aperture image estimates 1010 output at a output layer for a patient not used in training the network model. The graphical aperture images 1010 are the graphical aperture image estimates for a new patient.

Figure 11:
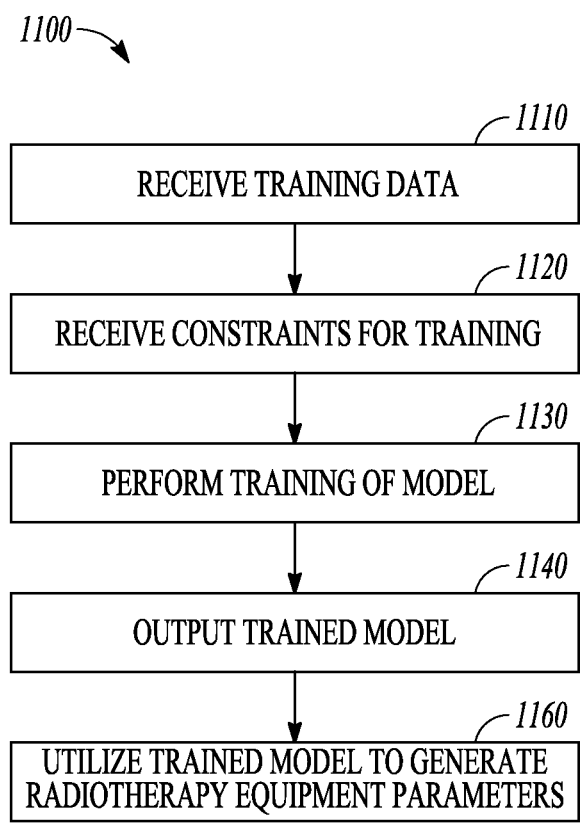
FIG. 11 illustrates an exemplary data flow for training and use of a machine learning model to generate radiotherapy equipment parameters according to some embodiments of the present disclosure.

FIG. 11 is a flowchart illustrating example operations of the image processing device 112 in performing process 1100, according to example embodiments. The process 1100 may be embodied in computer-readable instructions for execution by one or more processors such that the operations of the process 1100 may be performed in part or in whole by the functional components of the image processing device 112; accordingly, the process 1100 is described below by way of example with reference thereto. However, in other embodiments, at least some of the operations of the process 1100 may be deployed on various other hardware configurations. The process 1100 is therefore not intended to be limited to the image processing device 112 and can be implemented in whole, or in part, by any other component. Some or all of the operations of process 1100 can be in parallel, out of order, or entirely omitted.

At operation 1110, image processing device 112 receives training data. For example, image processing device 112 receives training data, which may include paired training data sets (e.g., input-output training pairs). Such training data may include a paired projection image of a patient anatomy at a given gantry angle with the ground truth machine parameters or graphical aperture image at that gantry angle.

At operation 1120, image processing device 112 receives constraints for training the model.

At operation 1130, image processing device 112 performs training of the model based on the received training data and constraints.

At operation 1150, image processing device 112 outputs the trained model. For example, image processing device 112 outputs the trained model to operate on a new set of projection images to estimate machine parameters and/or graphical aperture images corresponding to gantry angles of the projection images.

At operation 1160, image processing device 112 utilizes the trained model to generate machine parameters and/or graphical aperture images. For example, the image processing device 112 generates a graphical aperture image for a given gantry angle based on a projection image of a patient anatomy that represents a view of the anatomy from the given gantry angle. The image processing device 112 identifies a radiotherapy device type that will be used to treat the patient. The image processing device 112 obtains a function that computes control points (machine parameters) from a graphical aperture image. The image processing device 112 applies the generated graphical aperture image to the function to compute the control points (e.g., the leaf positions, jaw positions, and beam intensity) for the given gantry angle to be used during radiotherapy treatment of the patient. In some implementations, the image processing device 112 repeats the steps of obtaining the projection image from each gantry angle that is used during the radiotherapy treatment and generates the corresponding graphical aperture image for each of the obtained projection images. The image processing device 112 applies each of the generated graphical aperture images to the function that computes the control points for the given type of radiotherapy device that is used in order to compute the control points (e.g., the leaf positions, jaw positions, and beam intensity for each gantry angle that is used to treat the patient during one or more treatment fractions.

Figure 12:
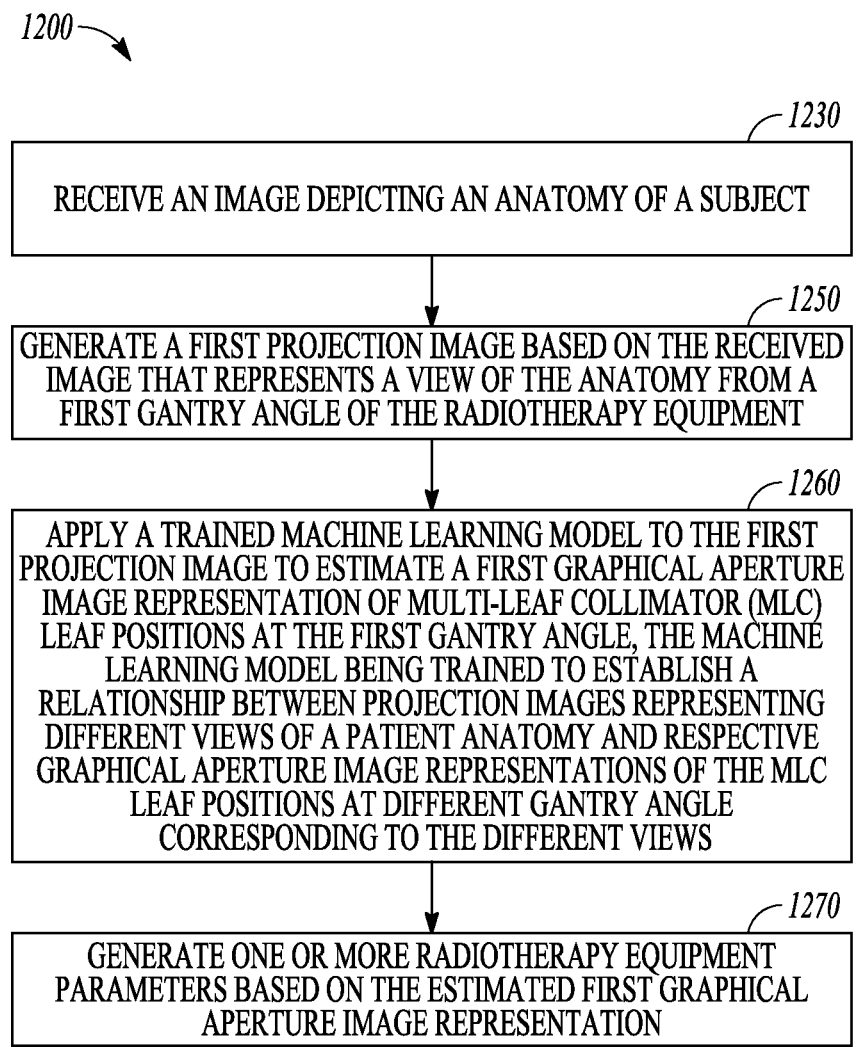
FIG. 12 illustrates a method for using trained deep learning to generate radiotherapy equipment parameters from a projection image of a given view of anatomy from a given gantry angle, according to some embodiments of the present disclosure.

FIG. 12 is a flowchart illustrating example operations of the image processing device 112 in performing process 1200, according to example embodiments. The process 1200 may be embodied in computer-readable instructions for execution by one or more processors such that the operations of the process 1200 may be performed in part or in whole by the functional components of the image processing device 112; accordingly, the process 1200 is described below by way of example with reference thereto. However, in other embodiments, at least some of the operations of the process 1200 may be deployed on various other hardware configurations. The process 1200 is therefore not intended to be limited to the image processing device 112 and can be implemented in whole, or in part, by any other component. Some or all of the operations of process 1200 can be in parallel, out of order, or entirely omitted.

At operation 1230, image processing device 112 receives an image depicting an anatomy of a subject.

At operation 1250, image processing device 112 generates a first projection image based on the received image that represents a view of the anatomy from a first gantry angle of the radiotherapy equipment.

At operation 1260, image processing device 112 applies a trained machine learning model to the first projection image to estimate a first graphical aperture image representation of MLC leaf positions at the first gantry angle, the machine learning model being trained to establish a relationship between projection images representing different views of a patient anatomy and respective graphical aperture image representations of the MLC leaf positions at different gantry angles corresponding to the different views.

At operation 1270, image processing device 112 generates one or more radiotherapy equipment parameters based on the estimated first graphical aperture image representation.

Figure 13:
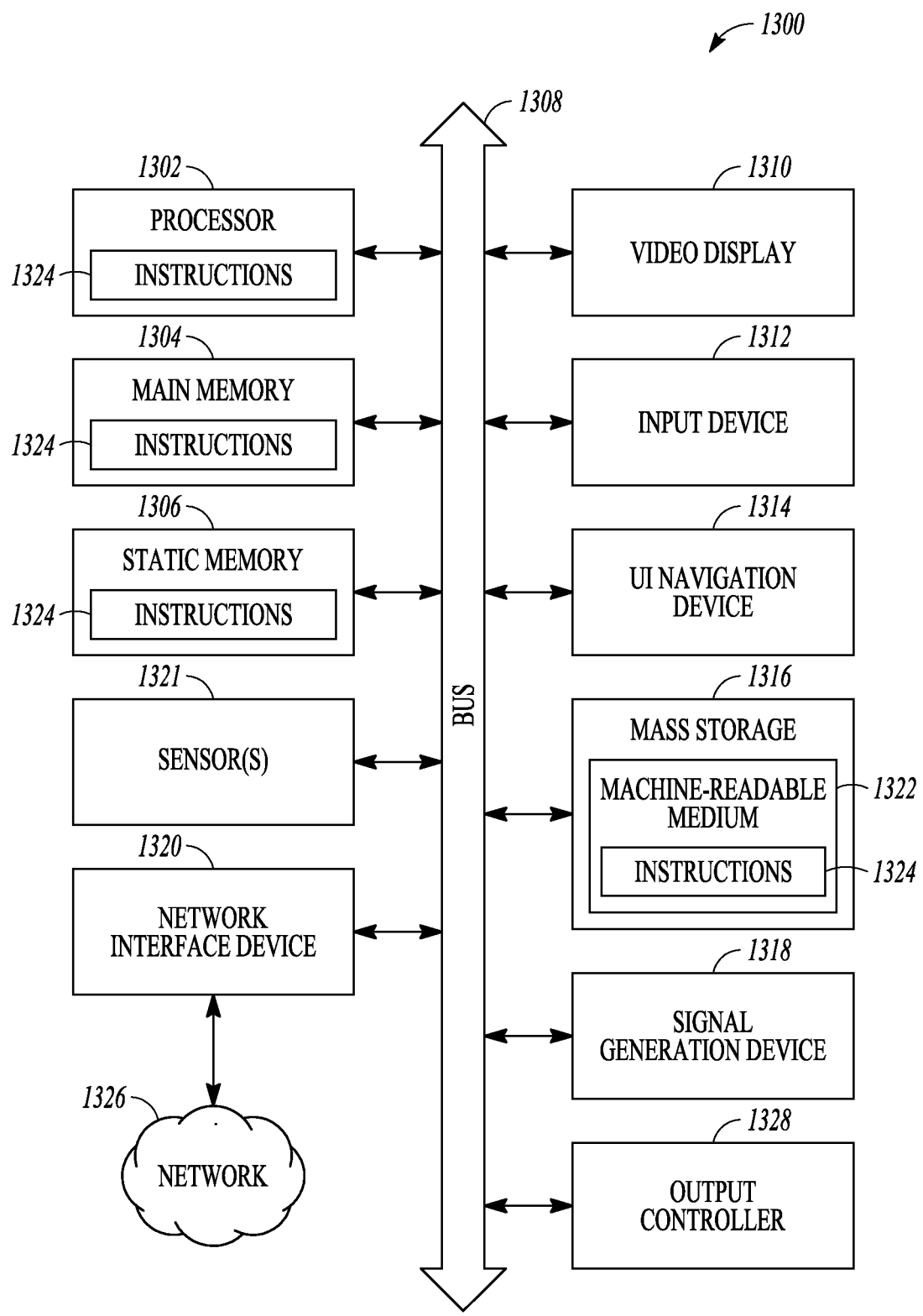
FIG. 13 illustrates an exemplary block diagram of a machine on which one or more of the methods as discussed herein can be implemented.

FIG. 13 illustrates a block diagram of an embodiment of a machine 1300 on which one or more of the methods as discussed herein can be implemented. In one or more embodiments, one or more items of the image processing device 112 can be implemented by the machine 1300. In alternative embodiments, the machine 1300 operates as a standalone device or may be connected (e.g., networked) to other machines. In one or more embodiments, the image processing device 112 can include one or more of the items of the machine 1300. In a networked deployment, the machine 1300 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1300 includes processing circuitry 1302 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 1321 (e.g., a transducer that converts one form of energy (e.g., light, heat, electrical, mechanical, or other energy) to another form of energy), or the like, or a combination thereof), a main memory 1304 and a static memory 1306, which communicate with each other via a bus 1308. The machine 1300 (e.g., computer system) may further include a video display unit 1310 (e.g., a liquid crystal display (LCD) or a cathode ray tube (CRT)). The machine 1300 also includes an alphanumeric input device 1312 (e.g., a keyboard), a user interface (UI) navigation device 1314 (e.g., a mouse), a disk drive or mass storage unit 1316, a signal generation device 1318 (e.g., a speaker), and a network interface device 1320.

The disk drive unit 1316 includes a machine-readable medium 1322 on which is stored one or more sets of instructions and data structures (e.g., software) 1324 embodying or utilized by any one or more of the methodologies or functions described herein. The instructions 1324 may also reside, completely or at least partially, within the main memory 1304 and/or within the processor 1302 during execution thereof by the machine 1300, the main memory 1304 and the processor 1302 also constituting machine-readable media.

The machine 1300 as illustrated includes an output controller 1328. The output controller 1328 manages data flow to/from the machine 1300. The output controller 1328 is sometimes called a device controller, with software that directly interacts with the output controller 1328 being called a device driver.

While the machine-readable medium 1322 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1324 may further be transmitted or received over a communications network 1326 using a transmission medium. The instructions 1324 may be transmitted using the network interface device 1320 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

The invention claimed is:

1. A method for generating radiotherapy treatment machine parameters based on projection images, the method comprising:
   receiving an image depicting an anatomy of a subject;
   generating a first projection image based on the received image that represents a view of the anatomy from a first gantry angle of the radiotherapy treatment machine;
   applying a trained machine learning model to the first projection image to estimate a first graphical aperture image representation of multi-leaf collimator (MLC) leaf positions at the first gantry angle, the machine learning model being trained to establish a relationship between projection images representing different views of a patient anatomy and respective graphical aperture image representations of the MLC leaf positions at different gantry angles corresponding to the different views; and
   generating one or more radiotherapy treatment machine parameters based on the estimated first graphical aperture image representation.

2. The method of claim 1, wherein the machine learning model comprises a deep convolution neural network.

3. The method of claim 1, further comprising training the machine learning model by adjusting one or more parameters of the machine learning model to minimize a cost function that includes a difference between predetermined sets of graphical aperture image representations of the MLC leaf positions corresponding to projection images representing different views of a patient anatomy and predicted sets of graphical aperture image representations of the MLC leaf positions at the different views.

4. The method of claim 1, wherein the one or more parameters include at least one of a gantry angle, an MLC jaw position, an MLC leaf position, or a radiation therapy beam intensity.

5. The method of claim 1, wherein receiving the image comprises receiving a three-dimensional image of the anatomy, further comprising generating a plurality of two-dimensional projection images including the first projection image that represent a plurality of two-dimensional views of the anatomy from a plurality of different gantry angles.

6. The method of claim 5, wherein the plurality of projection images represents views of the anatomy from 0 degrees to 360 degrees.

7. The method of claim 5, wherein the different gantry angles differ from one another by a predetermined amount.

8. The method of claim 1, further comprising:
   determining a type of the radiotherapy treatment machine, wherein the one or more radiotherapy treatment machine parameters are generated based on the type of the radiotherapy treatment machine.

9. The method of claim 1, wherein the image comprises a computed tomography (CT) image, a synthetic CT image, or a magnetic resonance (MR) image.

10. The method of claim 1, further comprising training the machine learning model by:
   obtaining the projection images representing different views of a patient anatomy from prior treatments;
   for each of the prior treatments:
   obtaining radiotherapy treatment machine parameter information representing MLC leaf positions at gantry angles corresponding to each of the different views and radiotherapy beam intensity corresponding to each of the projection images; and
   generating ground truth graphical aperture image representations based on the obtained radiotherapy treatment machine parameter information;
   aligning each of the generated ground truth graphical aperture image representations with the corresponding projection images; and
   adjusting one or more parameters of the machine learning model based on the aligned ground truth graphical aperture image representations and corresponding projection images.

11. The method of claim 10, wherein the one or more parameters of the machine learning model are adjusted by computing a deviation between a given graphical aperture image representation at a given one of the different views that is estimated based on a given projection image representing the given one of the different views with a corresponding one of the ground truth graphical aperture image representations for the given one of the different views.

12. The method of claim 1, further comprising computing a quality metric based on a comparison of the generated one or more radiotherapy treatment machine parameters with a set of parameters of a radiotherapy treatment plan.

13. The method of claim 1, further comprising computing a three-dimensional dose distribution based on the generated one or more radiotherapy treatment machine parameters.

14. The method of claim 1, wherein the first projection image is generated by ray tracing or Fourier reconstruction.

15. A method of training a machine learning model to estimate a graphical aperture image representation of multi-leaf collimator (MLC) leaf positions, the method comprising:
   obtaining a first projection image representing a first view of a patient anatomy from a previous treatment;
   obtaining radiotherapy treatment machine parameter information representing MLC leaf positions at a gantry angle corresponding to the first view of the first projection image;
   generating a first ground truth graphical aperture image representation based on the radiotherapy treatment machine parameter information; and
   adjusting one or more parameters of the machine learning model based on the first ground truth graphical aperture image representations and the first projection image.

16. The method of claim 15, wherein adjusting the one or more machine learning model parameters is performed by:
   applying the machine learning model to the first projection image to estimate a graphical aperture image representation of the MLC leaf positions at the gantry angle corresponding to the first view;
   computing a deviation between the estimated graphical aperture image representation and the first ground truth graphical image representation; and
   adjusting one or more machine learning model parameters based on the computed deviation.

17. The method of claim 15, wherein the radiotherapy treatment machine parameter information further includes radiotherapy beam intensity at the gantry angle, further comprising aligning the first ground truth graphical aperture image representation with the first projection image.

18. A system for generating radiotherapy treatment machine parameters based on projection images, the system comprising:
one or more processors for performing operations comprising:
receiving an image depicting an anatomy of a subject;
generating a first projection image based on the received image that represents a view of the anatomy from a first gantry angle of the radiotherapy treatment machine;
applying a trained machine learning model to the first projection image to estimate a first graphical aperture image representation of multi-leaf collimator (MLC) leaf positions at the first gantry angle, the machine learning model being trained to establish a relationship between projection images representing different views of a patient anatomy and respective graphical aperture image representations of the MLC leaf positions at different gantry angles corresponding to the different views; and
generating one or more radiotherapy treatment machine parameters based on the estimated first graphical aperture image representation.

19. The system of claim 18, wherein the operations further comprise training the machine learning model by adjusting one or more parameters of the machine learning model to minimize a cost function that includes a difference between predetermined sets of graphical aperture image representations of the MLC leaf positions corresponding to projection images representing different views of a patient anatomy and predicted sets of graphical aperture image representations of the MLC leaf positions at the different views.

20. The system of claim 18, wherein the operations further comprise receiving a three-dimensional image of the anatomy, further comprising generating a plurality of two-dimensional projection images including the first projection image that represent a plurality of two-dimensional views of the anatomy from a plurality of different gantry angles.

21. The system of claim 18, wherein the operations further comprise training the machine learning model by:
obtaining the projection images representing different views of a patient anatomy from prior treatments;
for each of the prior treatments:
obtaining radiotherapy treatment machine parameter information representing MLC leaf positions at gantry angles corresponding to each of the different views and radiotherapy beam intensity corresponding to each of the projection images; and
generating ground truth graphical aperture image representations based on the obtained radiotherapy treatment machine parameter information;
aligning each of the generated ground truth graphical aperture image representations with the corresponding projection images; and
adjusting one or more parameters of the machine learning model based on the aligned ground truth graphical aperture image representations and corresponding projection images.

22. A non-transitory machine-readable storage medium that includes instructions that, when executed by one or more processors of a machine, cause the machine to perform operations comprising:
receiving an image depicting an anatomy of a subject;
generating a first projection image based on the received image that represents a view of the anatomy from a first gantry angle of a radiotherapy treatment machine;
applying a machine learning model to the first projection image to estimate a first graphical aperture image representation of multi-leaf collimator (MLC) leaf positions at the first gantry angle, the machine learning model being trained to establish a relationship between projection images representing different views of a patient anatomy and respective graphical aperture image representations of the MLC leaf positions at different gantry angles corresponding to the different views; and
generating one or more radiotherapy treatment machine parameters based on the estimated first graphical aperture image representation.

23. The non-transitory machine-readable storage medium of claim 22, wherein the operations further comprise training the machine learning model by adjusting one or more parameters of the machine learning model to minimize a cost function that includes a difference between predetermined sets of graphical aperture image representations of the MLC leaf positions corresponding to projection images representing different views of a patient anatomy and predicted sets of graphical aperture image representations of the MLC leaf positions at the different views.

24. The non-transitory machine-readable storage medium of claim 22, wherein the operations further comprise receiving a three-dimensional image of the anatomy, further comprising generating a plurality of two-dimensional projection images including the first projection image that represent a plurality of two-dimensional views of the anatomy from a plurality of different gantry angles.

25. The non-transitory machine-readable storage medium of claim 22, wherein the operations further comprise training the machine learning model by:
obtaining the projection images representing different views of a patient anatomy from prior treatments;
for each of the prior treatments:
obtaining radiotherapy treatment machine parameter information representing MLC leaf positions at gantry angles corresponding to each of the different views and radiotherapy beam intensity corresponding to each of the projection images; and
generating ground truth graphical aperture image representations based on the obtained radiotherapy treatment machine parameter information;
aligning each of the generated ground truth graphical aperture image representations with the corresponding projection images; and
adjusting one or more parameters of the machine learning model based on the aligned ground truth graphical aperture image representations and corresponding projection images.

* * * * *